United States Patent [19]

Holley et al.

[11] Patent Number: 4,587,970
[45] Date of Patent: May 13, 1986

[54] TACHYCARDIA REVERSION PACER

[75] Inventors: Loraine K. Holley, Rockdale; Robert Evans, Chatswood, both of Australia

[73] Assignee: Telectronics N.V., Curacao, Netherlands Antilles

[21] Appl. No.: 693,592

[22] Filed: Jan. 22, 1985

[51] Int. Cl.$^4$ ............................................. A61A 1/36
[52] U.S. Cl. ............................................. 128/419 PG
[58] Field of Search ................... 128/419 PG, 419 PT

[56] References Cited

U.S. PATENT DOCUMENTS

| | | | |
|---|---|---|---|
| 3,939,844 | 2/1976 | Pequignot | 128/419 PG |
| 3,942,534 | 3/1976 | Allen et al. | 128/419 PG |
| 4,163,451 | 8/1979 | Lesnick et al. | 128/419 PG |
| 4,181,133 | 1/1980 | Kolenik et al. | 128/419 PG |
| 4,307,725 | 12/1981 | Sowton et al. | 128/419 PG |
| 4,384,585 | 5/1983 | Zipes | 128/419 PG |
| 4,388,927 | 6/1983 | Schober | 128/419 PG |
| 4,407,289 | 10/1983 | Nappolz et al. | 128/419 PG |
| 4,421,114 | 12/1983 | Berkovits et al. | 128/419 PG |
| 4,427,011 | 1/1984 | Spurrell et al. | 128/419 PG |
| 4,429,697 | 2/1984 | Nappholz et al. | 128/419 PG |
| 4,452,248 | 6/1984 | Keller, Jr. | 128/419 PG |
| 4,467,810 | 8/1984 | Vollmann | 128/419 PG |
| 4,473,078 | 9/1984 | Angel | 128/419 PG |
| 4,485,818 | 12/1984 | Leckrone et al. | 128/419 PG |
| 4,488,553 | 12/1984 | Nappholz et al. | 128/419 PG |
| 4,488,554 | 12/1984 | Nappholz et al. | 128/419 PG |
| 4,493,325 | 1/1985 | Hartlaub et al. | 128/419 PG |
| 4,515,161 | 5/1985 | Wittkampf et al. | 128/419 PG |
| 4,539,991 | 9/1985 | Boute et al. | 128/419 PG |
| 4,541,430 | 9/1985 | Elmquist et al. | 128/419 PG |
| 4,543,963 | 10/1985 | Gessman | 128/419 PG |

FOREIGN PATENT DOCUMENTS

| | | | |
|---|---|---|---|
| 3782 | 11/1982 | European Pat. Off. | 128/419 PG |
| 81209 | 6/1983 | European Pat. Off. | 128/419 PG |
| 87756 | 9/1983 | European Pat. Off. | 128/419 PG |
| 113176 | 7/1984 | European Pat. Off. | 128/419 PG |
| 2026870 | 2/1980 | United Kingdom | 128/419 PG |
| 2076655 | 12/1981 | United Kingdom | 128/419 PG |

OTHER PUBLICATIONS

Spurrell et al., "American Journal of Cardiology", vol. 49, Mar. 1982, pp. 753–760.
Dulk et al., "American Journal of Cardiology", vol. 52, 1983, pp. 731–738.
Kuck et al., "American Journal of Cardiology", vol. 54, 1984, pp. 550–554.

Primary Examiner—William E. Kamm
Attorney, Agent, or Firm—Gottlieb, Rackman & Reisman

[57] ABSTRACT

There is disclosed a tachycardia control pacer in which there is generated a sequence of pacing pulses at intervals which are a function of the effective refractory period intrinsically associated with the rate of the patient heartbeats. If the tachycardia episode is not terminated, another sequence of pulses is generated; however, the rate of the new sequence is decreased if at least one unevoked heartbeat was sensed during the preceding pacing pulse sequence and the rate is increased in the absence of any unevoked heartbeat having been sensed during the preceding pacing pulses sequence. Also, in order to smooth the transition between the fast pulses used to terminate the tachycardia episode and subsequent beating in sinus rhythm, pacing pulses continue to be generated at increasing pacing intervals until they merge into standby pacing.

122 Claims, 13 Drawing Figures

FIG. 1
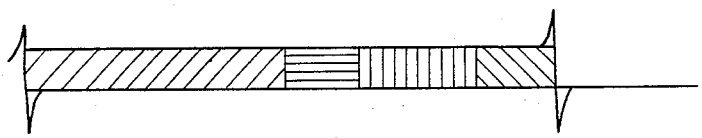
TIMING ZONES BETWEEN R WAVES
REFRACTORY ZONE 
TERMINATION ZONE 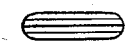
RESET ZONE 
COLLISION ZONE 

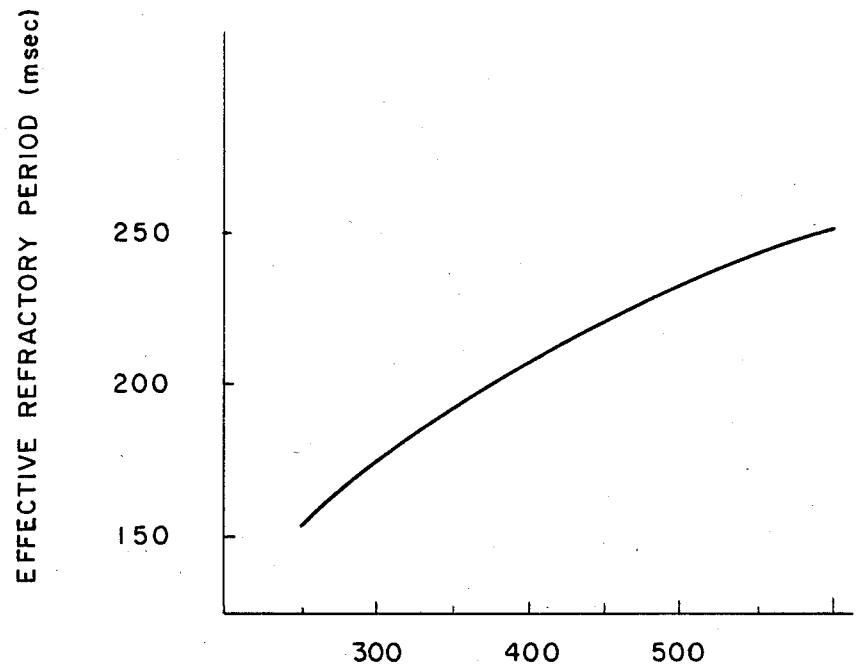
FIG. 2 PHYSIOLOGICAL RELATIONSHIP BETWEEN EFFECTIVE REFRACTORY PERIOD AND TACHYCARDIA CYCLE LENGTH
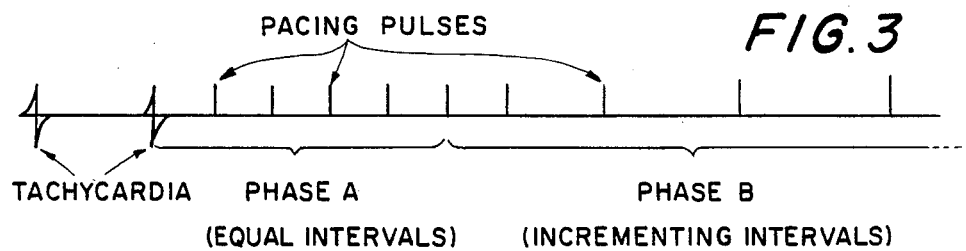

RESET

STO

ST2

ST3

ST4/ST5

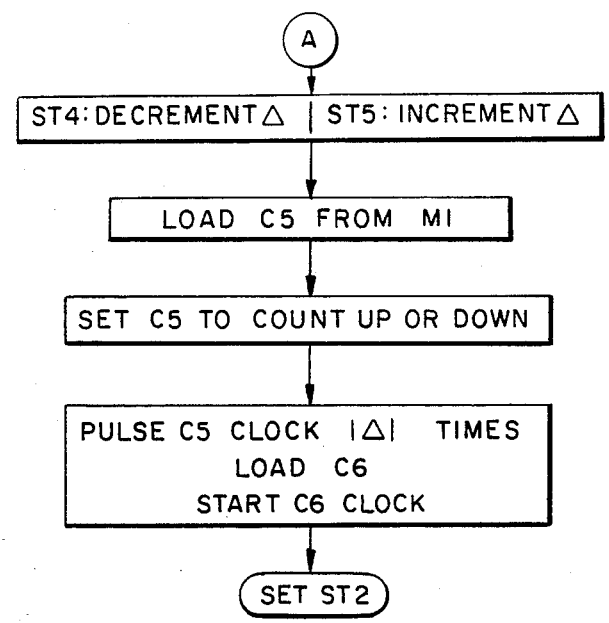
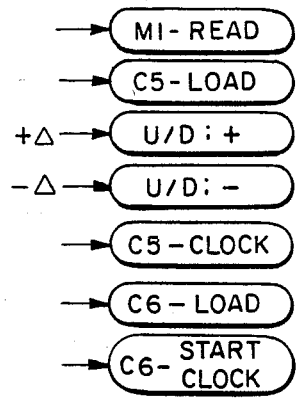
FIG. 11B
ST4/ST5
(CONT.)
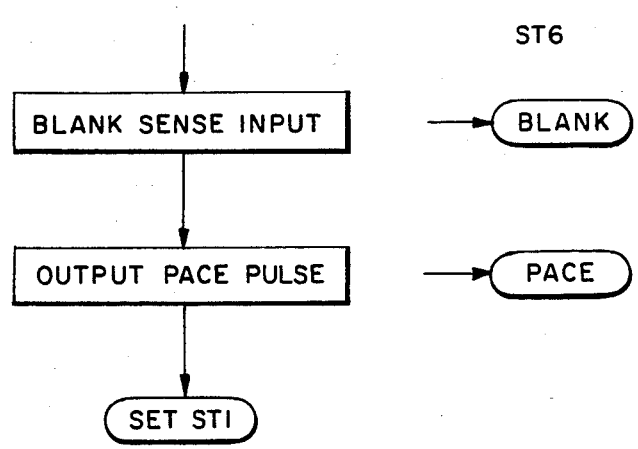
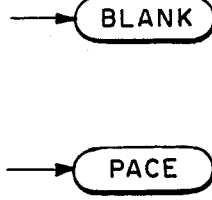
FIG. 12
ST6

TACHYCARDIA REVERSION PACER

This invention relates to tachycardia reversion pacers, and more particularly to implantable pacers for rapidly terminating a tachycardia episode.

Many strategies have been devised for pacing a patient's heart in order to terminate a tachycardia episode. One commercially available system is that disclosed in U.S. Pat. No. 4,390,021 issued on June 28, 1983 to Spurrell et al. In that pacer, two pulses are generated following confirmation of tachycardia; the first pulse follows the last heartbeat used in the confirmation process by an "initial delay", and the second pulse follows the initial delay by a "coupled interval". In the absence of tachycardia reversion, one or both of the initial delay and the coupled interval are changed. Both time periods are thus "scanned", and the successful time intervals are retained for use when tachycardia is next confirmed, the scanning process being initiated once again only if the two retained values are no longer effective. The Spurrell et al system is not as fast-acting in terminating a tachycardia episode as it might be for several reasons. Perhaps the most important is that the initial time intervals used following tachycardia confirmation are totally unrelated to the rate of the patient's heartbeats.

Implicit in the design of the Spurrell et al pacer is the recognition that more than one pacing pulse will usually be required to terminate a tachycardia episode. Especially in the case of ventricular tachycardia, a single pulse, no matter when it is generated following tachycardia confirmation, is likely to be unsuccessful. The reason for this is that the tachycardia is caused by a localized circus movement, and it can be thought of as generating a series of wavefronts which travel away from it. The pacer electrode, typically in the right ventricle, similarly generates a series of wavefronts, one for each pacing pulse. Colliding wavefronts cancel each other, but if the pacing rate is faster than the tachycardia rate, then successive collisions get closer and closer to the heart tissue which is causing the problem. Only if enough pacing pulses are generated will one of them reach the affected area and disrupt the circus movement. Of course, the wavefront, or source pacing pulse, which is effective in terminating the tachycardia episode must be timed properly relative to the self-sustaining beating of the heart. It is for this reason that it has been recognized in the past that not only is a burst of pulses most desired, but the rate of the pulses in each burst should be scanned from episode to episode, until a successful rate is found. Thereafter, that rate can be used to terminate the next tachycardia episode as well, with scanning being initiated only if it is later found that that rate is no longer effective. A "scanning burst" tachycardia control pacer of this type is disclosed in Nappholz et al U.S. Pat. No. 4,398,536 which issued on Aug. 16, 1983. An even more efficacious system is disclosed in Nappholz et al U.S. Pat. No. 4,406,287 which issued on Sept. 27, 1983, in which not only is the rate of each burst scanned, but the number of pulses in each burst is scanned as well.

All three of these systems "work" on a hit-and-miss basis. Once an effective rate is determined, it is immediately used following the next tachycardia confirmation in the hope that it will be successful again. But if it is not, there is no way to predict which rate will be successful, and therefore to use it. The scanning simply takes its course until a successful rate is found. The systems are "nonadaptive" in the sense that the pacing intervals are not related to the tachycardia cycle length. The tachycardia cycle length, i.e., the time between successive heartbeats, is used only to confirm tachycardia in the first place; it is not used in any way to determine the pacing interval.

Another prior art patent of interest is U.S. Pat. No. 4,408,606 in the name of Spurrell et al, which patent issued on Oct. 11, 1983. In the pacer disclosed in this patent, the time interval between the last heartbeat used in the confirmation process and the first pacing pulse is indeed related to the rate of the heartbeats. The time interval is a bit shorter than the tachycardia cycle length. However, the pulses in the ensuing burst are not generated at a fixed rate. Instead, the burst is more accurately characterized as a "chirp", with the rate of the pulses in the burst speeding up from beginning to end. Another scanning system which searches for a "window of termination" by a scanning process is disclosed in Sowton U.S. Pat. No. 4,312,356 which issued on Jan. 26, 1982. The Sowton scanning system allows a pulse to be generated earlier or later in a cycle.

It is thus clear that prior art workers did recognize that the rate of the heartbeats should somehow be used, at least in the first instance, to determine the rate of the pacing pulses generated in an attempt to terminate the tachycardia episode. But it is not the rate of the heartbeats which should be the directly controlling parameter. We have discovered that the important parameter is the effective refractory period. While the effective refractory period can be determined from the heartbeat rate with the use of a predetermined function, there is no simple linear relationship. It is for this reason that prior art workers, while they relied on the heartbeat rate in determining the pacing rate, did not use it effectively.

As will be explained in greater detail below, there are really four timing zones between successive ventricular contractions. (Similar remarks apply to atrial contractions in the case of a pacer used to terminate atrial tachycardia.) In the first time zone, the heart is refractory to any pacing pulse, and the pulse is totally ineffective. Reversion will occur if a pacing pulse is applied during the second time zone, the "termination" zone. Ideally, the first pacing pulse in any burst should be applied as soon as possible after the effective refractory period, i.e., at the start of the termination zone. The interval between the last heartbeat (R wave) used to confirm tachycardia and the first pacing pulse should then be used, in the preferred embodiment of our invention, to define all of the pacing intervals in the ensuing burst.

In this regard, the closest prior art to the present invention is Baker U.S. Pat. No. 4,280,502 which issued on July 28, 1981. The Baker anti-tachycardia pacing system introduces a single pulse interval following a tachycardia event. The pacing pulse is applied to a first electrode, and a second electrode is then used to sense a subsequent cardiac event. The interval is adjusted so that the refractory period is determined. Once the refractory period is determined, a second pulse is introduced, with the interval between the first pulse and the second being scanned during sucessive cycles until reversion occurs. There are many differences between our system and that of Baker, as will become apparent below. One big difference is that Baker requires two electrodes because it is not possible to sense a cardiac response so soon after a pulse stimulus, both on the same electrode. For a tachycardia control pacer to be practical, at least at the present time, the same electrode should be used for both pacing and sensing.

Another major difference between our system and that of Baker is that while in both the effective refractory period is in effect determined by means of a scanning process, it is determined faster in our system because our scanning begins at a better place. In both systems the tachycardia cycle length is measured, and in both systems the first pacing interval which is used is calculated based upon the measured tachycardia cycle length. The difference is that Baker's pacing interval is a direct function of the tachycardia cycle length, while in our system the pacing interval is determined only indirectly, although in a predetermined manner, from the tachycardia cycle length. Instead of simply calculating the "first try" from the heartbeat rate, there is stored in the pacer, in the form of a table, a predetermined function of effective refractory period versus heartbeat rate. How that function is determined will be described in detail below, but it is not linear. The velocity of a wavefront in the ventricular myocardium varies with the rate at which the heart is beating. The longer the interval between heartbeats the longer the effective refractory period, but the rate at which the effective refractory period increases does not remain constant; the rate (first derivative) decreases with increasing tachycardia cycle length. The effective refractory period as a predetermined function of pacing rate is determined in advance on the basis of a sample population. [It is contemplated that in the future the predetermined function will be determined on an individual patient basis.] Baker does not base his pacing interval on the effective refractory period, but rather only on the heartbeat rate. We utilize the heartbeat rate to determine the effective refractory period, and it is the effective refractory period which is used to determine the pacing interval. (It should not be mistakenly thought that the effective refractory period can be determined only from the pacing rate. In accordance with the principles of our invention, the effective refractory period can be a predetermined function of other things as well, such as the Q-T interval in an electrocardiogram signal.)

There are many other differences between our system and that of Baker. In Baker, the pacing intervals in any two-pulse burst are not necessarily the same; in our system, in the preferred embodiment, the pacing intervals in any multi-pulse burst used to terminate tachycardia are the same. In Baker, if the first pulse is found not to capture the heart, the scanning process involving the second pulse is aborted, and instead the system begins all over again to determine the effective refractory period; in our system, cycling does not begin all over again simply because one or more pulses in a sequence fail to capture the heart.

Thus one basic distinction between our method of operating a tachycardia control pacer and those of the prior art, especially that of Baker, is that the pacing interval which defines our pulse burst is not simply a function of the rate at which the patient heartbeats are occurring; rather, the pacing interval is a predetermined function which is based upon the physiological relationship of effective refractory period and tachycardia rate. In the preferred embodiment of the invention, an empirical relationship is actually prestored in the pacer, the empirical relationship being determined based upon experiments performed upon a sample population. Although we have in common with Baker the recognition that effective refractory period is a key parameter, the remaining steps of our methodology have almost nothing in common with the prior art. Although all of the features of our invention will be described below, at this point the basic processing steps in the preferred embodiment will be summarized.

The predefined function of effective refractory period versus tachycardia cycle length is used to determine the pacing interval which characterizes all of the pacing pulses in the first burst following tachycardia confirmation. The pacing interval selected is one which hopefully will cause the first pacing pulse to be generated shortly after the end of the effective refractory period; that pulse, or more probably one of the succeeding pulses, will hopefully terminate the tachycardia episode.

Following the generation of each pacing pulse, the conventional sense amplifier is blanked in the usual way so that the pacing pulse itself will not be sensed as a heartbeat. Suppose, now, that a heartbeat is sensed during the course of the pulse burst, following the blanking interval after any pulse. The heartbeat which was thus sensed could not have been an evoked response. This, in turn, means that the pulse burst in progress is not capturing the heart as the pacing intervals are shorter than the effective refractory period, and that the heart is still beating independently of the pacing pulses. Another pulse burst is generated, but with a longer pacing interval, i.e., a slower rate, in the hope that the new pacing interval will be longer than the effective refractory period. One advantage of scanning in the upward direction is that even if the first pacing interval used was too short, it should not take too many additional bursts before the pacing interval is longer than the effective refractory period.

In the preferred embodiment of the invention, another burst, with a longer pacing interval, is not generated immediately when a heartbeat which is not an evoked response is sensed. As soon as such an event is sensed the pulse burst in progress is aborted, but another burst is not generated until after tachycardia is confirmed in the usual way by counting a predetermined number of fast heartbeats. What should also be appreciated is that the new pacing interval is not simply the old pacing interval increased by some predetermined amount.

Even though the first burst did not terminate the tachycardia episode, it is certainly possible that it may have caused the rate of the heartbeats to change, i.e., the tachycardia cycle length to shorten or lengthen. For this reason, the predetermined function of effective refractory period versus tachycardia cycle length is used once again to determine a new pacing interval based upon the current beating of the patient's heart. But the failure of the previous burst to terminate the episode is an indication that the predetermined function no longer applies. Body chemistry, exercise, and a multitude of other "inputs" can affect the effective refractory period versus tachycardia cycle length plot. Even though a new pacing interval is determined from the latest tachycardia cycle length, it is assumed that the entire plot has to be shifted upward because of the sensing of an unevoked response during the first pulse burst. For this reason, the newly determined pacing interval is incremented, and the new pulse burst is generated at a slower rate. (Instead of using a fixed increment, the increase could be computed based on a percentage of the previous or even new pacing interval.)

This process continues until no unevoked response is sensed during a pulse burst. It might be thought that pacing should then stop since it can be presumed that the tachycardia episode has been terminated. This is generally what has been done in the prior art. However, we provide a second phase of pacing in which the pacing pulses are generated at slower and slower rates. The reason for doing this is to avoid an abrupt change in heartbeat rate from the fast rate of the pacing pulse sequence to the slower sinus rhythm. In the second pacing phase, the pacing intervals successively lengthen; in fact, as they lengthen the pacing merges into conventional standby pacing.

The next question is how to treat the sensing of an unevoked heartbeat during the generation of the pacing pulses in what we call the second phase, or phase B, the phase during which the pacing intervals successively lengthen. An unevoked heartbeat could be due to the heart beating in sinus rhythm, or it could be an indication of tachycardia. The routine for confirming tachycardia is invoked in the usual way. If the heart is beating in sinus rhythm, no further pacing is required. On the other hand, if tachycardia has been confirmed again, another sequence of "phase A", or fixed-rate, tachycardia-terminating pacing is called for. But at what rate?

During phase A pacing, a fixed number of pulses were generated. If no unevoked response was sensed, it means that all pulses in the phase A sequence resulted in heart capture. This, in turn, is an indication that the pacing interval was longer than the effective refractory period. Unlike the case where an unevoked response is sensed during phase A pacing, there is no need to increase the pacing interval if tachycardia is reconfirmed during phase B pacing. The fact that the tachycardia persists is now an indication that the pacing interval used during phase A pacing was too long; the pacing interval was even longer than the sum of the refractory and termination zones and, while the pacing pulses captured the heart, they did not terminate the tachycardia. For this reason what is now required is a shorter pacing interval, i.e., phase A pacing at a higher rate.

Once again, the predetermined function is used to determine a new pacing interval; based upon the latest measured tachycardia cycle length, a new pacing interval is computed. But because the previous phase A pacing sequence did not terminate the tachycardia, it is an indication that the plot of effective refractory period versus tachycardia cycle length for one reason or another has shifted; the plot has moved downward. For this reason, the newly computed pacing interval is decremented, and it is the decremented pacing interval which is used to generate pacing pulses at a fixed rate in an attempt to terminate the tachycardia.

While it is preferred that the pulses during phase A pacing occur at a fixed rate, it may not be essential that they do so. What is important, at least for the fastest possible tachycardia reversion, is that the pacing pulses be generated at intervals which are a predetermined function based upon the physiological relationship of effective refractory period and tachycardia rate. In its broadest sense, the pacing pulses are generated at intervals which are a function of the effective refractory period intrinsically associated with the rate of the heartbeat. The phase-B aspect of our invention, of course, has application even in systems in which the phase-A pulsing is not intrinsically associated with the tachycardia cycle length.

In effect, what a pacer constructed in accordance with the principles of our invention does is to generate a sequence of pulses at a rate which is a function of the rate at which the patient heartbeats are occurring during a tachycardia episode, with the pacing rate for successive pulse sequences being modified by decreasing it if at least one unevoked heartbeat is sensed during the preceding pacing pulse sequence, or increasing it in the absence of any unevoked heartbeat during the preceding pacing pulse sequence. Preferably, the hunting process involves use of the predetermined function following every tachycardia confirmation and the evaluation of a new tachycardia cycle length, with the newly computed pacing interval being incremented or decremented depending upon whether or not an unevoked heartbeat was sensed during the preceding pacing pulse sequence used to terminate the tachycardia.

Further objects, features and advantages of our invention will become apparent upon consideration of the following detailed description in conjunction with the drawings, in which:

FIG. 1 depicts the timing zones between two successive R waves of a tachycardia episode;

FIG. 2 depicts a plot of effective refractory period versus tachycardia cycle length, i.e., the physiological relationship discussed above which is used to determine the pacing intervals;

FIG. 3 depicts the last two R waves of a tachycardia episode, followed by the pacing pulses during the phase A and phase B sequences;

FIGS. 6-12 are flow charts which depict the method of our invention as implemented in the pacer of FIG. 4.

Figure 4:
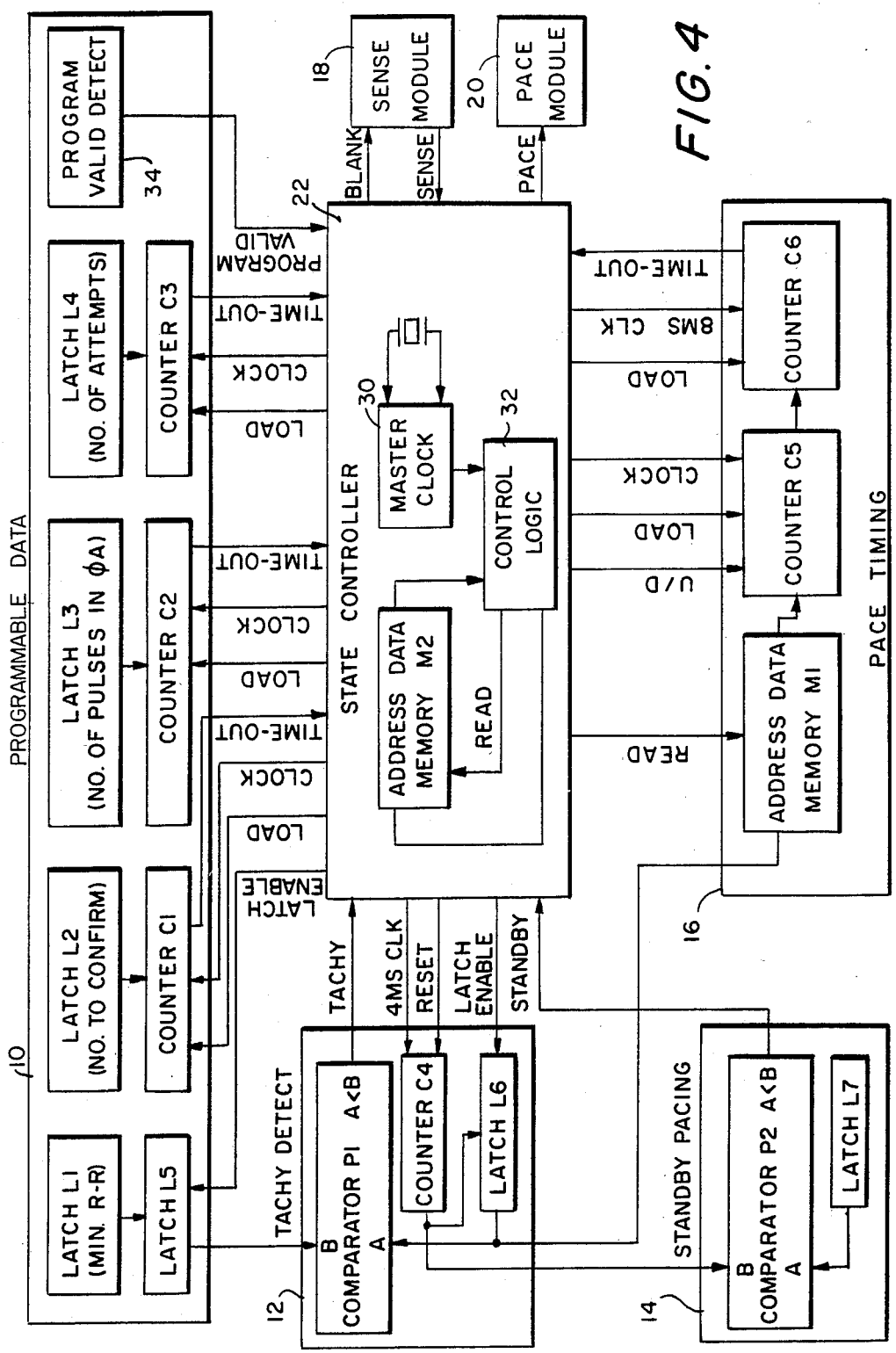
FIG. 4 depicts a pacer constructed in accordance with the principles of our invention.

Electrophysiological studies have permitted certain characteristic timing zones to be documented, and these are shown in FIG. 1. The refractory zone is that in which a pacing pulse will have no effect on the heart tissue; following depolarization, the tissue must repolarize before an electrical stimulus has any effect on it. The termination zone is the only region in which a stimulus is likely to terminate a tachycardia episode. A pulse falling in the reset zone will not generally terminate the episode, although it will introduce a single, short interval followed by the original tachycardia interval, thus "resetting" or "advancing" the tachycardia. A pacing pulse falling in the collision zone will produce what is known as a fusion beat but will not otherwise affect the tachycardia.

FIG. 2 depicts the physiological relationship between effective refractory period and tachycardia cycle length. The curve obviously varies from patient to patient. Ideally, any pacemaker operated in accordance with the principles of our invention should be programmed to reflect the plot applicable to the particular patient. However, at least with the state of present-day technology it is not feasible to conduct a study on each individual patient and to pre-program his pacer accordingly. For this reason, a plot has been made for a sample population, and the "average" is used in the practice of our invention. For any measured tachycardia cycle length (the inverse of the heartbeat rate), the effective refractory period can be determined from the plot. If the pacing interval is then made slightly longer than the effective refractory period, the first pacing pulse will fall just outside the refractory zone, and thus termination of the tachycardia episode with maximum speed is facilitated.

The plot of FIG. 2 represents the predetermined function referred to above. The plot of FIG. 2 can be determined as follows. A number of representative patients are selected. It is possible to select several different patient groups and to develop an "average" plot or function for each group or type of patient, and then preprogram the pacer of a particular patient in accordance with the plot for the patient group which represents the closest match. In any event, each patient in the sample group is paced at many different tachycardia rates. For each rate, the last pacing interval in the sequence is scanned to determine the effective refractory interval for that rate. By scanning the last pacing interval is meant that the interval is slowly decreased until a heart response is not evoked; that, in turn, means that the pacing pulse fell at the end of the refractory period. Thus for each tachycardia rate, and for each patient, it is possible to determine the effective refractory interval. By averaging the data determined for all of the patient-rate pairs, it is possible to compute a function of effective refractory period versus tachycardia rate, i.e., the plot of FIG. 2. Because the plot is an average, it can be expected that if the first pacing pulse is generated following the last heartbeat used to confirm tachycardia after an interval equal to the effective refractory period as determined from FIG. 2, then for many patients that pacing pulse will fall in the refractory zone. For this reason, the pacing interval which is pre-programmed or computed based on the plot of FIG. 2 is slightly greater, e.g., 30 milliseconds, than the mean value which is shown. Actually, based on empirical results, we cause the pacing interval which is computed to be equal to the effective refractory period determined from the sample patient population but increased by about 30 milliseconds at fast rates, with the increase gradually increasing and reaching about 50 milliseconds at the slower rates. In all cases we have found that the effective refractory period, and therefore the pacing interval, increases with a decreasing patient heartbeat rate but with a decreasing slope. It is contemplated that ultimately a pacemaker itself will perform the measurements on a particular patient and thereby devise a predetermined function which is unique and most efficacious for the particular patient.

When the predetermined function is stored in a pacer in the form of a table, obviously every coordinate pair of the plot cannot be stored. It has been found sufficient to store the pacing intervals applicable to respective tachycardia cycle lengths at 25-millisecond intervals, with a straight-forward process of interpolation being used to compute the pacing interval applicable to any tachycardia cycle length which is not a multiple of 25 milliseconds.

Before actually describing the pacer and method of our invention, it will be helpful to appreciate the two phases of the pacing as depicted in FIG. 3. At the left of FIG. 3 are shown two R waves, the last two of the several used to confirm a tachycardia episode. There follows a series of five pacing pulses in phase A. The number of pacing pulses is variable, as will be described below, but all pacing intervals in phase A in the preferred embodiment of the invention are equal. The selected interval, based on the predetermined function represented in FIG. 2, not only applies to all pulses which are generated in phase A, but also to the spacing between the last R wave and the first pacing pulse. During phase B pacing, the pacing intervals gradually lengthen, ultimately merging into standby pacing as will be described in detail below.

THE PACER OF FIG. 4

The pacer of our invention is shown in FIG. 4. It consists of conventional blocks and sub-blocks commonly used in digital systems and especially in those under microprocessor control. Block 10, containing the Programmable Data, includes a number of latches and counters, all to be discussed below. The Tachy Detect block 12 is used in the process of confirming the existence of a tachycardia episode. The block measures the time interval between successive heartbeats and determines whether the interval is less than a prescribed limit which is stored in the programmable data block 10.

The Standby Pacing block 14 controls conventional standby pacing, and the Pace Timing block 16 controls the inter-pulse intervals in phase-A and phase-B pacing.

Sense Module block 18 is a conventional circuit for sensing a P wave or an R wave. When a signal is sensed, the sense output line is energized. Following the generation of a corresponding pacing pulse, the blank input line is energized to inhibit operation of the Sense Module, a feature well known in the pacing art. The Pace Module 20 is a conventional pulse generator, triggered by a signal applied to its pace input. The Sense and Pace Modules have their respective input and output connected to the same electrode lead (not shown), with the pacemaker case serving as the indifferent lead as is conventional practice.

All of the system sequencing is controlled by State Controller 22. The State Controller can be operated in each of the states depicted in FIG. 5: the reset state, or any of states ST0-ST6. Each state is associated with a particular task. A transition from one state to another depends upon the present state and the existence of a certain condition. For example, referring to FIG. 5, if the system is in state ST5 and the sinus rhythm condition is determined to exist, the system switches to state ST1. The State Controller is of conventional design, and includes three blocks: master clock 30, memory M2, and control logic 32. The control logic applies an address to the address input of the memory (random access), and when the read input of the memory is pulsed the data stored at the respective address is furnished to the control logic. The master clock controls all of the system timing in the usual fashion. The address furnished to memory M2 corresponds with the present system state. The data furnished back to the control logic represents all of the states which may be entered from the present state, together with the conditions which will control the respective sequencing. For example, referring to FIG. 5, when the system is in state ST2, the address applied on the address bus is associated with state ST2. The data which is read from memory M2 identifies three possible succeeding states, ST0, ST3 and ST5, together with the three respective input conditions which control the respective state transitions, C3 time-out, C2 time-out and QRS. The control logic waits for one of the three input conditions to occur, following which a transition is made to the new state.

Master clock 30 operates at a 16-KHz rate. The control logic includes a set of dividers for deriving 4-millisecond and 8-millisecond clocks, the purpose of which will be described below.

Block 10 includes 4 latches L1-L4 which store four programmable parameters. The latches are loaded by program valid detect circuit 34, a conventional pacer module. When valid program parameters are detected via the programming link, the program valid input of state controller 22 is pulsed to inform the state controller that valid program parameters have been sensed. At the same time, the parameters are stored in the four latches. The only parameters shown in the system of FIG. 4 in block 10 are those required for an understanding of the present invention. Other parameters which are standard in the pacer art, such as pacing pulse width, sensitivity, etc. are not shown because they are not necessary for an understanding of the present invention.

Latch L1 contains the minimum R—R interval (tachycardia cycle length) which is accepted as sinus rhythm. Nine bits are used for this purpose. Any inter-beat interval whose duration is less than the value stored in latch L1 is representative of a tachycardia episode. However, tachycardia is not confirmed until a predetermined number of these short inter-pulse intervals are sensed in succession. Latch L2 contains the number of consecutive R—R intervals which must be shorter than the tachycardia cycle length which is stored in latch L1 in order for the pacer to confirm tachycardia. Only four bits are required for latch L2 since rarely will there be a requirement to sense more than 15 rapid heartbeats in order to confirm tachycardia.

Latch L3 is a four-bit latch which contains the number of pulses which are generated during phase-A pacing. Five such pulses are shown in FIG. 3, but up to 15 may be programmed. Latch L4 contains the "number of attempts", that is, the number of consecutive times that the pacer will try to revert a tachycardia episode if sinus rhythm does not occur. The latch has four bits, and thus at most fifteen attempts may be made to terminate tachycardia. In the illustrative embodiment of the invention, once the maximum number of attempts have been made, the pacer ceases to operate until it is reprogrammed.

Associated with latches L2, L3 and L4 are three counters—C1, C2 and C3. Each of these counters has loaded in it the data in the respective latch when the respective load input is pulsed. Each counter is a four-bit presettable binary down counter. The count in each counter is decremented when the respective clock input is pulsed. Similarly, when a counter is decremented down to zero, it energizes its respective time-out conductor to inform the State Controller. The time-out conductor of each counter is really what is known as a carry output. The time-out label is used because the pulsing of one of the conductors represents the end of a sequence.

Latch L5, when its latch enable input is pulsed, simply has transferred to it the minimum R—R interval which is stored in latch L1. The output of latch L5 is applied to the B input of 9-bit comparator P1 in the Tachy Detect block 12. The reason that the output of latch L1 is not extended directly to the B input of the comparator is that by using latch L5 in an intermediate capacity, the pacer can actually be programmed without disrupting the current processing. Even though the program valid detect circuit 34 may load a new minimum R—R interval in latch L1, the previous contents of the latch are stored in latch L5 so that the current processing may continue. It is only the next time that the latch enable input to latch L5 is pulsed that the new value will be used.

The Tachy Detect block 12 is used to determine when a short inter-beat interval of a tachycardia episode has occurred. Counter C4 is a nine-bit binary up counter which is clocked at a 4-millisecond rate. The count of counter C4 thus represents the number of 4-millisecond intervals which have occurred following the last reset pulse. The latch enable input of latch L6 is pulsed when an R wave is sensed; the contents of counter C4 are transferred to latch L6 and the counter is then reset. Thus latch L6 represents the most recent R—R interval. The output of the latch is applied to the A input of comparator P1. If the value in latch L6 is less than the interval represented by latch L5, then the output of comparator P1 is energized, the output being labelled "tachy". It should be noted that the output of counter C4 is not extended directly to the A input of the comparator. The reason for this is is that at the start of every R—R interval, counter C4 will represent a count which is always less than that stored in latch L5. It is only at the end of the R—R interval that a check is made to see whether the most recent R wave is too soon after the preceding one.

Because counter C4 is clocked at 4-millisecond intervals, its accuracy in measuring the R—R interval is reduced as the R—R interval decreases. However, even for a heart rate as high as 300 beats per minute, the error is only about + or −2%, a value which is certainly acceptable.

The Standby Pacing module 14 is used to determine whether the heart rate has fallen below a preset minimum value. The preset value, in terms of standby interval, is stored in 9-bit latch L7. In the illustrative embodiment of the invention it is factory set, but the value could be programmable if desired. The preset value is applied to the A input of 9-bit comparator P2. The current count of counter C4 is applied to the B input of comparator P2. As long as the current count, representing the R—R interval in progress, is less than the standby interval stored in latch L7, the output of comparator P2, the standby lead, remains low. But as soon as the count of counter C4 exceeds the standby interval, the standby lead goes high in potential to inform the State Controller that a heartbeat has not occurred for a number of milliseconds equal to the standby value. It is at this time that a pacing pulse is generated—not to terminate tachycardia, but rather to stimulate a heartbeat. Since counter C4 is clocked at 4-millisecond intervals and it includes nine stages, the maximum count which the counter can represent is 512×4 or 2048 milliseconds. This is equivalent to a heart rate of about 29 beats per minute, certainly a value which can accommodate all desired standby pacing rates.

The output of latch L6 represents the R—R interval which preceded the last heartbeat. The output of the latch is applied to the address input of memory M1 in the Pace Timing block 16. When the read input of the memory is pulsed by the State Controller, a data value is applied to the input of counter C5. The memory stores pacing intervals, based upon the plot of FIG. 2. The address inputs represent the tachycardia cycle length values, at 25-millisecond intervals. For each address, the data output is the pacing interval which, as discussed above, is slightly greater than the corresponding effective refractory period. It is a feature of our invention that during phase-A pacing the initial pacing interval which is selected is that which will allow the first pacing pulse to be generated just following the effective refractory period. Since the effective refractory period is a predetermined function of the R—R interval, and the pacing interval is a function of the effective refractory period, the R—R interval can be used to access memory M1 to derive the pacing interval which should be used. The use of a memory in this fashion is a simple way of implementing the predetermined function.

The pacing interval for memory M1 is loaded into counter C5 when its load input is pulsed by the State Controller. The state of the U/D (up/down) lead determines whether the count in counter C5 is incremented or decremented when its clock input is pulsed. Counter C6 is loaded from the count in counter C5 when the load input of counter C6 is pulsed. Counter C6 is decremented at 8-millisecond intervals when the 8-millisecond clock pulses are applied to its clock input. When the counter counts down to zero, it energizes its time-out conductor. Counters C5 and C6, both of which are 8-bit devices, control the inter-pulse intervals shown in FIG. 3, and their detailed operations will be described below.

The remaining figures are flow charts which depict the system operation. In each case a particular flow chart should be read in conjunction with the state diagram of FIG. 5, since the state diagram illustrates the transitions from one state to the next. It should also be noted that the various flow charts include two kinds of symbols in the left and right margins. In the left margin there are represented the input parameters, while in the right margin there are represented the outputs. These will be described in detail below as the sequencing in each state is described.

RESET STATE—FIG. 6

Figure 6:
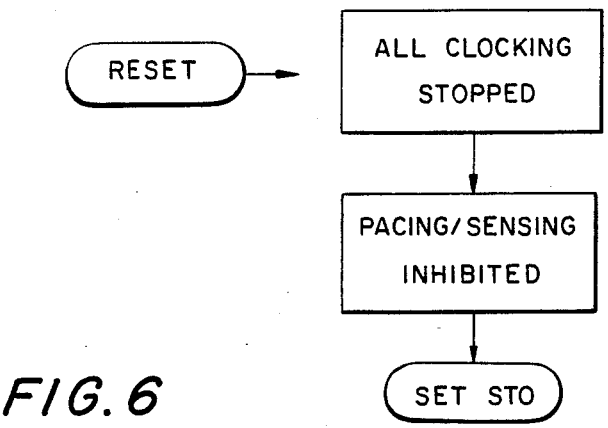

The reset state is a conventional "power-on" state, but it is also the result of a master reset, for example, should a conventional pacer programmer program the pacer to stop functioning. When a reset signal is sensed by the control logic, as indicated by the reset input in the left margin of FIG. 6, all clocking is stopped. Furthermore, the sense and pace modules 18, 20 are inhibited from operating. The pacer is turned off and the system enters state ST0.

STATE ST0—FIG. 7

In state ST0, the pacer waits until it is programmed. When the program valid line of FIG. 4 goes high, represented in FIG. 7 as a program valid input, several things take place. First, counter C4 is reset, and this is indicated as one of the outputs in the flow chart of FIG. 7. Counter C4 is the counter which times R—R intervals. Next, counter C1 is loaded with a count representing the number of consecutive short R—R intervals which must be sensed in order to confirm tachycardia. Then latch L5 is loaded, upon the pulsing by the State Controller of the latch enable line, with a count representing the minimum R—R interval which is considered to be sinus rhythm. A variable delta is used later on to keep track of the direction and degree of movement of the plot of FIG. 2 required to represent a new pacing interval as a function of the current tachycardia cycle length. The variable delta, basically a count, is initialized in state ST0 following reprogramming.

The sense module 18 is then switched on so that beating of the patient's heart can be detected. Also, the clocks are switched on although the only clock of importance at this time is the 4-millisecond clock which advances the count in counter C4 at 4-millisecond intervals in order to time the R—R intervals.

Figure 5:
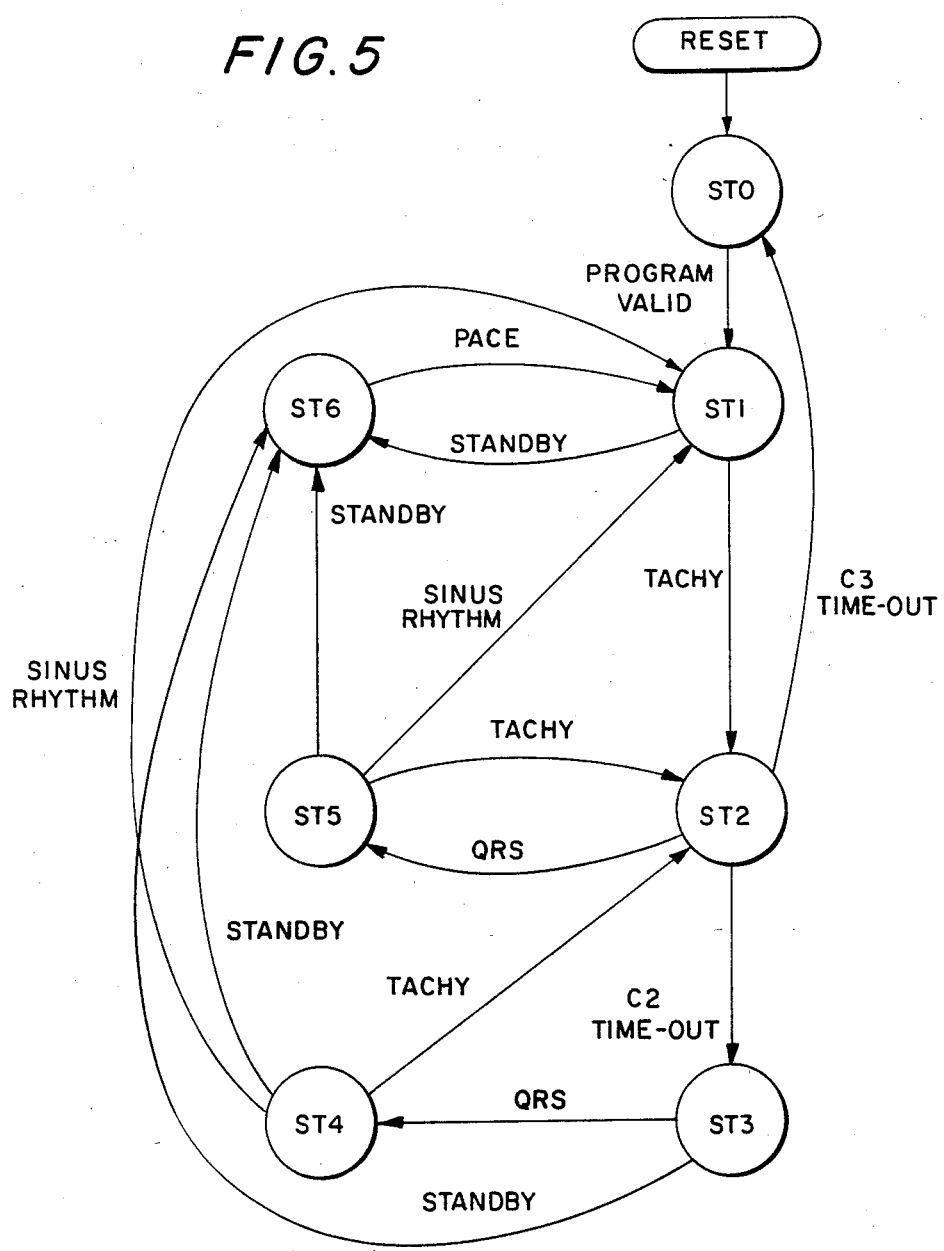
FIG. 5 is a state diagram which characterizes the method of our invention.
Figure 7:
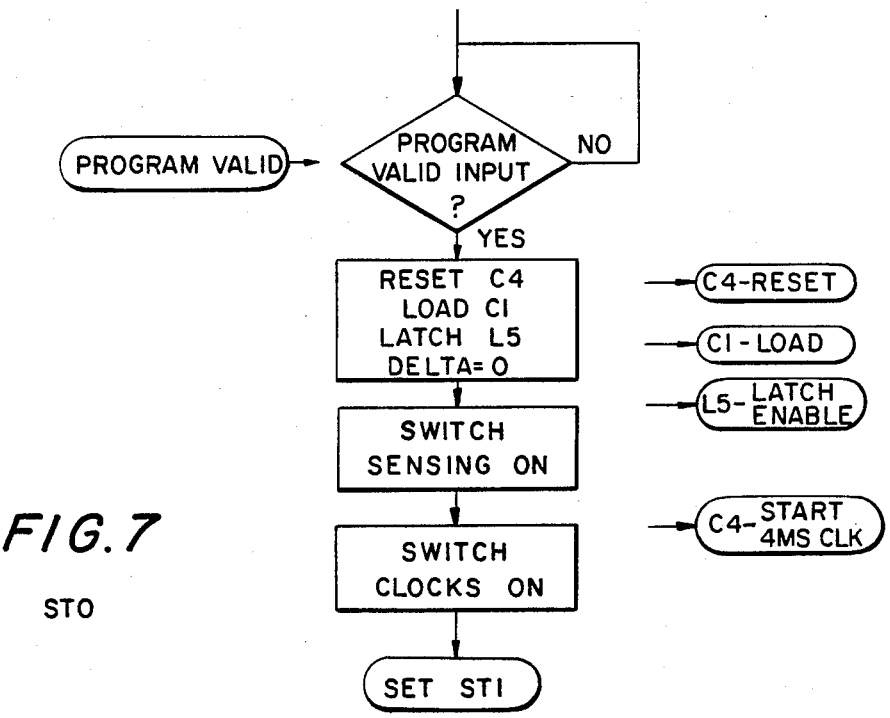

As indicated in the state diagram of FIG. 5, and as also indicated at the end of the flow chart of FIG. 7, after the initialization of the system in this manner there is a transition to state ST1.

STATE ST1—FIG. 8

In state ST1, the function of the system is to sense heartbeats, i.e., QRS complexes (or R waves). There are really only two possibilities, one resulting in a transition to state ST2, and the other resulting in a transition to state ST6, as indicated on the state diagram of FIG. 5. If the predetermined number of consecutive fast heartbeats are sensed, otherwise known as tachycardia confirmation, the system switches to state ST2. As long as fast heartbeats are occurring, but before the number of such consecutive beats has reached the number contained in latch L2 of FIG. 4, the system simply continues to count, by decrementing counter C1, the number of fast heartbeats which have occurred. The other possibility is for a heartbeat not to be sensed for the standby interval, that is, the time period from the last heartbeat to exceed the standby interval which is represented in latch L7. In such a case, the system switches to state ST6 so that a pacing pulse may be generated to cause the heart to beat. In short, in state ST1 the pacer senses whether the heart is beating so fast that tachycardia has developed, or whether the heart is beating so slowly that a pacing pulse is required to stimulate it.

Figure 8:
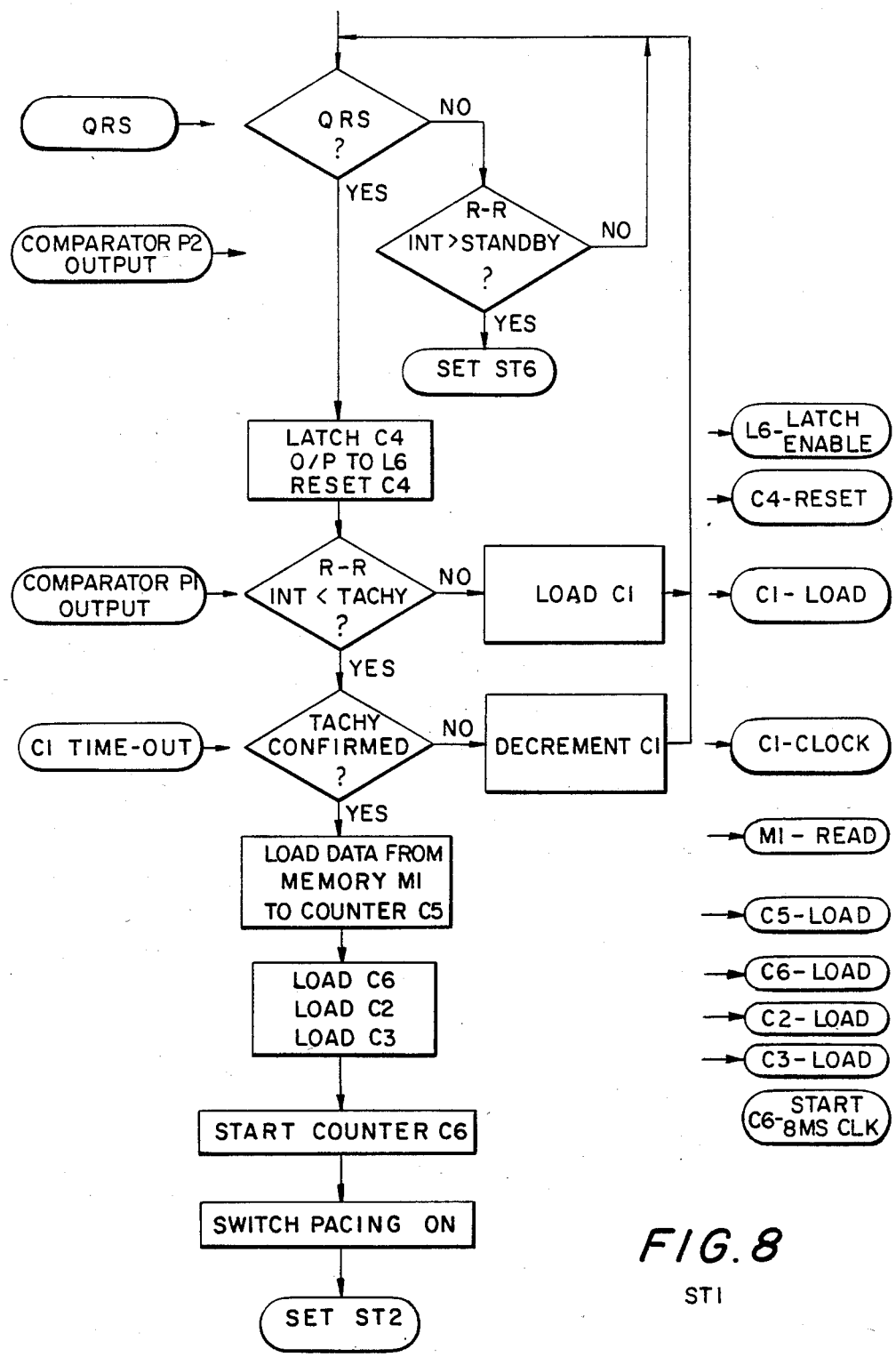

As indicated in the flow chart of FIG. 8, the pacer waits until a QRS complex is sensed. As long as a heartbeat has not been sensed, the pacer tests whether the R—R interval in progress exceeds the standby interval. It does this by continuously comparing the count in counter C4 with the value stored in latch L7. As indicated in FIG. 8, the relevant "input" is the output of comparator P2. If the comparator output goes high, indicating that the R—R interval in progress exceeds the standby interval, the system switches to state ST6. As will become apparent below, in this state practically nothing happens other than the generation of a pacing pulse.

If the output of comparator P2 does not go high, the system simply continues to check for the appearance of an R wave. Each time that the heart beats, the output of counter C4 is latched into latch L6. As indicated on FIG. 8, the latch enable input of latch L6 is energized. In this manner the most recent R—R interval is stored in the latch. Immediately thereafter, counter C4 is reset so that another R—R interval can be measured.

With latch L6 now representing the most recent R—R interval, a test is performed to see whether that interval is less than the "tachy" rate, that is, whether the R—R interval just measured is less than the interval represented in latch L5. If it is not, the output of comparator P1 remains low, and this is an indication that no action should be taken. The number of consecutive fast heartbeats which have been detected is represented by the decremented count in counter C1. If an R—R interval is sensed which is not long enough to be considered part of a tachycardia episode, counter C1 should be returned to its original count, the count represented by latch L2. For this reason, if the output of comparator P1 remains low, the load input to counter C1 is pulsed. The count in counter C1 is restored to the original value in latch L2 and the system continues to monitor heartbeats.

On the other hand, if the output of comparator P1 is high, indicating that the most recent R—R interval is shorter than the minimum interval required to confirm tachycardia, the system examines the time-out output of counter C1. If the counter was previously decremented down to zero, the most recent fast heartbeat confirms the presence of a tachycardia episode. If, on the other hand, counter C1 has not timed out, its clock input is pulsed. This results in the decrementing of the count, after which the system returns to monitor heartbeats.

Typically, latch L2 might be programmed to represent 8 fast heartbeats in order to confirm tachycardia. Following a time-out, the read input of memory M1 is pulsed. The address input of the memory is derived from the output of latch L6, the latch output representing the most recent R—R interval. The memory is thus read and the data which is loaded into counter C5, with the pulsing of the load input of the counter, represents the pacing interval for the current tachycardia rate.

It should be appreciated that the pacing interval which is read from memory M1 is a function only of the last R—R interval in the series which is used to confirm tachycardia. The pacing interval, which is based upon the effective refractory period which itself is a predetermined function of the tachycardia cycle length, is in the illustrative embodiment of the invention a function only of the last R—R interval. It would be possible, however, to make the pacing interval a function of the average of all of the R—R intervals which make up the tachycardia confirmation process, although it is preferred that the last R—R interval control the pacing interval.

The system will soon enter phase A of pacing in order to terminate the tachycardia episode. But before it does so, a few set-up operations are performed. First, counter C6 has its load input pulsed so that the same count (pacing interval) stored in counter C5 is stored in counter C6 as well. Counter C2 then has its load input pulsed so that the number stored in latch L3 is transferred to counter C2. The number thus stored in counter C2 represents the number of pulses in the first phase of the subsequent pacing. Similarly, the load input of counter C3 is pulsed so that this counter represents the total number of attempts which should be made in order to terminate the tachycardia.

Thereafter, the 8-millisecond clock input of counter C6 is pulsed at 8-millisecond intervals. That is what is meant in FIG. 8 by the step "start counter C6". The reason for doing this will become apparent below. Next, the Pace Module 20 is turned on so that pacing pulses can be generated, although the pulses are actually generated at times to be described below. The system then makes a transition to state ST2, the state during which the pulses are actually generated in an attempt to terminate tachycardia. As shown on FIG. 5, it is the "tachy" condition which controls the state transition, the "tachy" condition being represented by time-out of counter C1. Similarly, on FIG. 8, an affirmative answer to the "tachy confirmed" question leads to the state transition.

STATE ST2—FIG. 9

Figure 9:
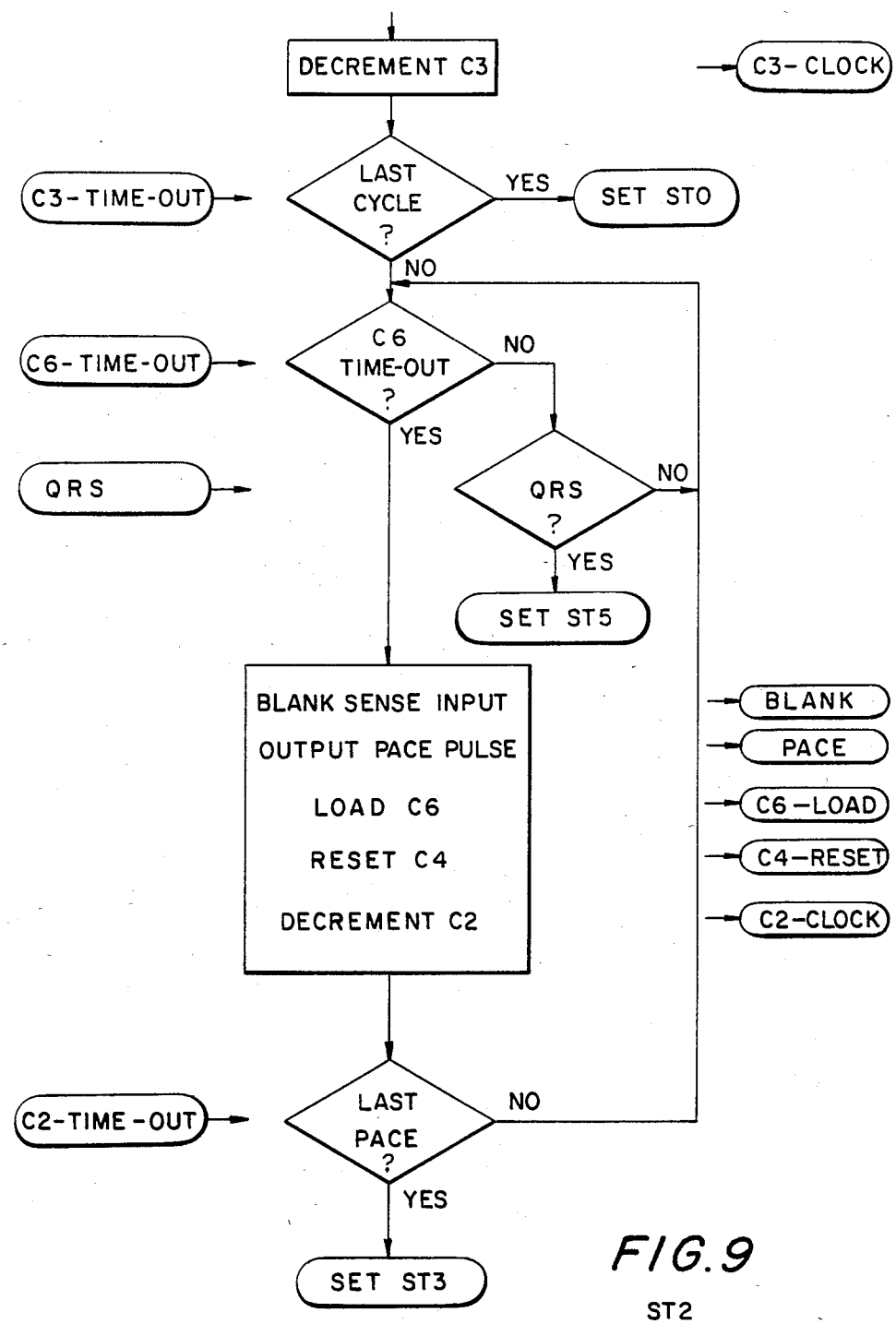

On entering state ST2, counter C3 is decremented with the pulsing of the clock input of the counter. Since an attempt will now be made to terminate the tachycardia episode, the counter is decremented. As described above, after the maximum number of attempts have been made, without success, the system "gives up". This is indicated on the state diagram of FIG. 5 by a C3 time-out which returns the system to state ST0. Referring to FIG. 9, after counter C3 is decremented, its time-out output is examined. If a time-out has occurred, the system switches to state ST0, at which point it simply waits to be programmed. [This is not to exclude the possibility of a complete recycling in which case another entire sequence would be begun.]

Counter C5 originally contains the pacing interval to be used in phase A pacing. At the end of the sequencing in state ST1, counter C6 was loaded with this same value. Counter C6 is now pulsed once every 8 milliseconds. The system waits until counter C6 times out. It will time out at the end of every pacing interval. (Counter C6 will be described below as being initialized prior to every pacing interval during phase A pacing.) As long as the system is waiting for the time-out, the sense module 18 checks to see whether an R wave takes place. As long as one does not, the system continues to wait for a time-out of counter C6. But if an R wave is sensed, it means that despite the generation of pacing pulses, the heart has beat on its own; the sensed heartbeat could not have resulted from a pacing pulse since the sense module is blanked following each pacing pulse so that the heartbeat which results from that pulse will not be sensed. Although the cycling could continue, there is no need to allow it to continue since it is clear that the pacing pulses are occurring at such a fast rate that they are not capturing the heart. The system immediately switches to state ST5, as indicated in both of FIGS. 5 and 9. It does not matter when during the phase A pacing the heartbeat is detected. Whenever it is detected, the pacing sequence is aborted and the system switches to state ST5 during which the pacing interval will be increased after which phase A pacing will be tried again.

Assuming, however, that a heartbeat is not detected, when counter C6 times out it is an indication that the pacing interval has expired. Before a pacing pulse is actually generated, the blank input of the Sense Module is energized so that sensing will be disabled for 100 milliseconds; as far as the Sense Module is concerned, the pacing pulse now to be generated will go undetected. Then the pace input of Pace Module 20 is energized.

Now that a pacing pulse has been generated, the pacing interval must be timed again so that the next pulse in the phase A sequence can be generated. All that is required for this is that counter C6 be loaded once again from counter C5, and all this takes is the pulsing of the load input of counter C6. Another pacing interval is timed automatically with the generation of the 8-millisecond clocks.

After the setting up of counter C6 for the timing of another pacing interval, counter C4 is reset. This counter measures R—R intervals, and since a heartbeat has (hopefully) taken place as a result of the pacing pulse, the counter must be reset. Counter C2 is then decremented with the pulsing of its clock input. This is the counter whose count is decremented to indicate that another pulse in the phase A sequence has been generated. The last step in the state ST2 processing is to examine whether the last pacing pulse in the phase A sequence has been generated, that is, whether a time-out of counter C2 has occurred. If it has not, the system continues to wait for the next time-out of counter C6 at which time the next pacing pulse in the phase A sequence will be generated. But if the last pulse in the phase A sequence has been generated, indicated by a time-out of counter C2, the system switches to state ST3 as indicated on both of FIGS. 5 and 9. It is in state ST3 that the phase B pulses of FIG. 3 are generated.

STATE ST3—FIG. 10

The phase B pacing is not required as part of the tachycardia termination process. Rather, the phase B pacing provides for a smooth transition in the rate of the heartbeats—from the fast rate controlled by the phase A pacing, up to the slower rate of a sinus rhythm or even that of standby pacing.

At the end of the sequencing in state ST2, counter C6 is loaded with the pacing interval in the usual way. In state ST3, as indicated on FIG. 10, the system waits for a time-out of counter C6. While waiting for a time-out, heartbeats are still monitored. If a heartbeat is sensed, as indicated by a QRS input on FIG. 10, the system switches to state ST4. There are two reasons why the heart may have beat other than as an evoked response to a pacing pulse generated in the phase B sequence. The heart may be beating in sinus rhythm, or the tachycardia may not have been reverted (even though no unevoked response was sensed during the phase A pacing). It is even possible that the heart, although it beat this once, will not beat again on its own in which case standby pacing will be required. All of this will be sorted out in state ST4.

Figure 10:
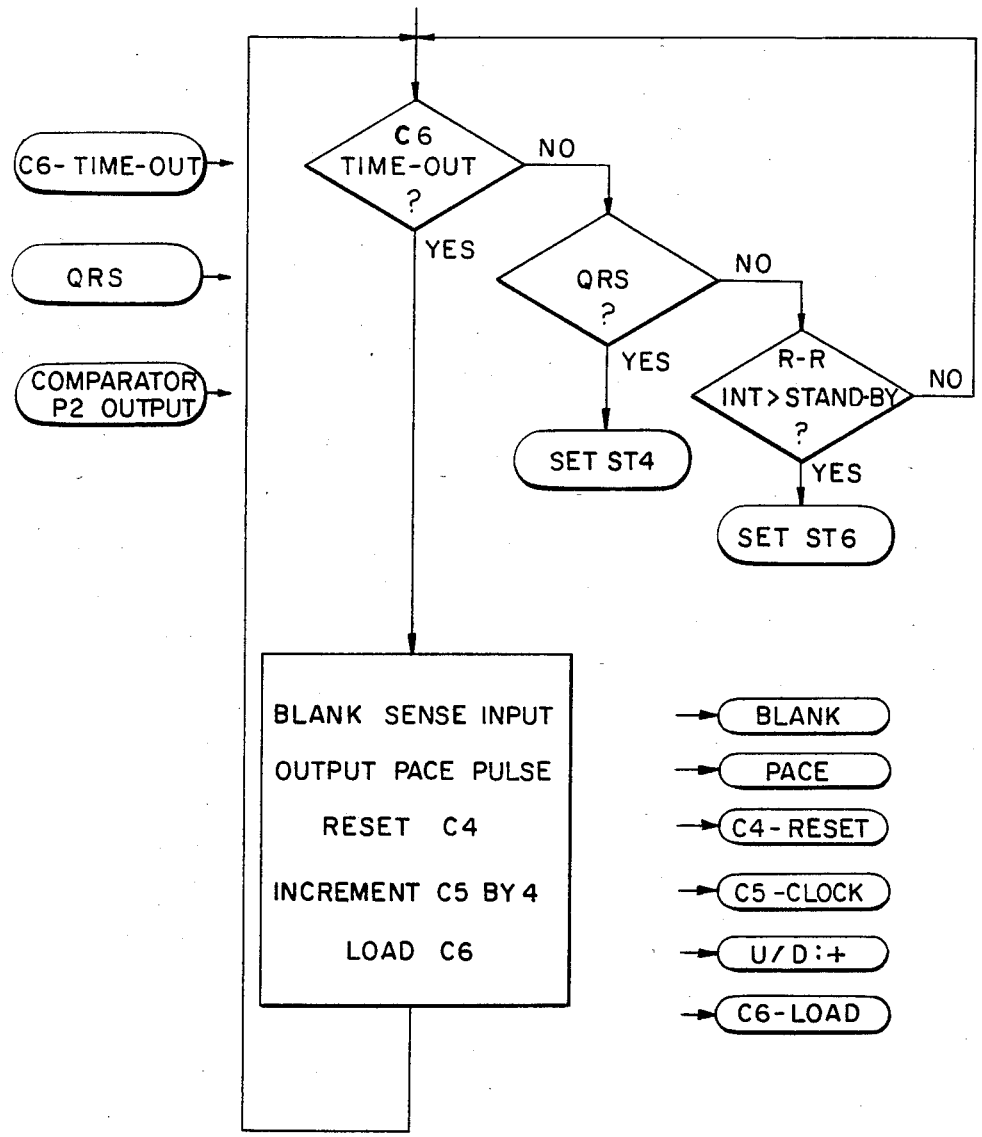

Returning to the QRS test in FIG. 10, as long as a heartbeat is not sensed, and while counter C6 continues to time the pacing interval, comparator P2 continuously monitors the count in counter C4. It will be recalled that counter C4 was reset toward the end of the processing in state ST2. The last pacing pulse generated in the phase A sequence presumably stimulated a heartbeat, and counter C4 times an R—R interval in the usual way. If the output of comparator P2 goes high, to indicate that the R—R interval in process exceeds the standby interval stored in latch L7, the system switches to state ST6. This is the state, as described above, during which a pacing pulse is generated in order to stimulate the heart. If the standby interval has not been exceeded, the system simply continues to wait for the counter C6 time-out.

When counter C6 times out, a pulse in the phase B sequence is generated. It should be noted that counter C6 was initially loaded with the original pacing interval, so that the first pulse in the phase B sequence occurs after a pacing interval which is equal to the pacing interval of all of the pulses during the phase A sequence. It is of no moment whether this first pulse is considered to be part of the phase A pulsing or the phase B pulsing.

Now that a pulse must be generated, the sense module is first blanked, after which the pace module is triggered. Counter C4 is then reset in the usual way since R—R interval timing is always required.

The system then readies itself for the next pulse in the phase B sequence. The clock input of counter C5 is pulsed rapidly four times in succession while the U/D lead is held high to control an "up" count. Counter C5 is clocked at 16 kHz, or once every 62.5 microseconds, to ensure that the time taken to increase its count by 4 is minimal compared to the pacing interval. After the count is increased by 4, the load input of counter C6 is pulsed. Thus there is stored in counter C6 the previous pacing interval increased by 4. This, in turn, requires an extra 4 of the 8-millisecond clock pulses in order to achieve a time-out of counter C6. This means that the pacing intervals during phase B are successively longer by 32 milliseconds.

The cycling then continues with the timing of counter C6. It should be noted that there is no exit at the bottom of the flow chart of FIG. 10. There are only two exits, and those have already been described—the transition to state ST4 when a QRS complex is sensed, and the transition to state ST6 when the heart has not beat for longer than standby interval. This is because the phase B pacing merges into standby pacing. The pacing intervals get longer and longer. If the heart is beating in sinus rhythm, a QRS input will be sensed. It is in state ST4, as described above, that it is finally determined what is going on. On the other hand, if the heart does not beat on its own, it will be the pulses in the phase B sequence which stimulate the heartbeats. Eventually, the pacing interval in the phase B sequence will get so long that it will be the standby interval which will become dominant (shorter), in which case it will be the Standby Pacing module 14 which causes the sysem to enter state ST6 at which time a pacing pulse is generated.

STATES ST4 AND ST5—FIGS. 11A AND 11B

Both of states ST4 and ST5 are depicted in the same flow chart because it is only toward the end of the sequencing that the two states differ.

Before describing the processing in states ST4 and ST5, it will be helpful to review how the system reaches these two states in the first place. The only way to reach state ST4 is by sensing a QRS complex while in state ST3. As just described in connection with FIG. 10, the system was in the process of generating phase B pulses when the heart beat on its own, i.e., an unevoked response was sensed. That could be due to the pacing interval having gotten so long that the heart, now beating in sinus rhythm, beat on its own before the next pacing pulse was generated. It is also possible, especially toward the start of the phase B pacing, that the heart beat on its own because the tachycardia episode had not been terminated. Even though there were no unevoked responses during phase A pacing, that is, all phase A pacing pulses captured the heart, the tachycardia episode may not have been terminated, in which case a QRS complex will be sensed as soon as a phase B pacing interval is longer than the tachycardia cycle length.

The system can reach state ST5 only when a QRS complex is sensed during phase A pacing, as indicated on FIGS. 5 and 9. There is little question in this case, however, about what has happened. Since the sense amplifier is blanked with the generation of each pacing pulse, the sensing of a heartbeat must represent an unevoked response. This means that the pacing pulses are not capturing the heart, and it is highly unlikely that the tachycardia episode has been terminated. In all probability, the pacing interval is too short, i.e., shorter than the effective refractory period. What must be done in state ST5 is to increase the pacing interval. This is not to say that it is impossible for the tachycardia to have been reverted. On the contrary, the heart may be beating in sinus rhythm. Alternatively, it is even possible that the heart has stopped beating altogether, in which case standby pacing is required.

Referring to FIG. 5, in both of states ST4 and ST5, there are three exits. If the heart has stopped beating (always a possibility to be taken into account) and the current R—R interval exceeds the standby interval, then in both cases what is required is a pacing pulse. The standby output lead of block 14 of FIG. 4 goes high at the expiration of the standby interval and, whether the system is in state ST4 or state ST5, a transition is made to state ST6. It is in state ST6 that a pacing pulse is generated when one is required to stimulate the heart. Similarly, if it is determined in state ST4 or state ST5 that the heart is beating in sinus rhythm, then the system switches to state ST1 in which case the cycling begins all over again with the monitoring of the heart. [There is no "sinus rhythm" output on the flow chart of FIG. 11, even though two such indications appear on the state diagram of FIG. 5. The "sinus rhythm" labels on FIG. 5 simply represent the sensing of a beat in sinus rhythm, as will be described below.]

Similarly, referring to FIG. 5 it will be seen that if a "tachy" condition exists (time-out of counter C1), then a transition is made from each of states ST4 and ST5 to state ST2. The most recent energization of the output of comparator P1 is an indication that the latest R—R interval is shorter than the minimum R—R interval stored in latch L1. This means that the heart is beating too fast and that, if the tachycardia episode still persists, the phase A pacing should be repeated, but with a different pacing interval. It is here that the processing in states ST4 and ST5 differ. If the system is in state ST5, it means that it never completed phase A pacing which, in turn, means that the most recent pacing pulse in a phase A sequence did not capture the heart. The pacing interval must therefore be increased. But if the system is in state ST4, it means that phase B pacing was taking place, and that no unevoked responses were sensed during the complete phase A pacing pulse sequence. Since the phase A pulses did capture the heart but were ineffective in terminating the tachycardia, the indications are that the pacing interval was too long. The first pacing pulse probably fell past the termination zone, rather than before it. It is for this reason that the pacing interval is decremented before phase A pacing is resumed.

Figure 11A:
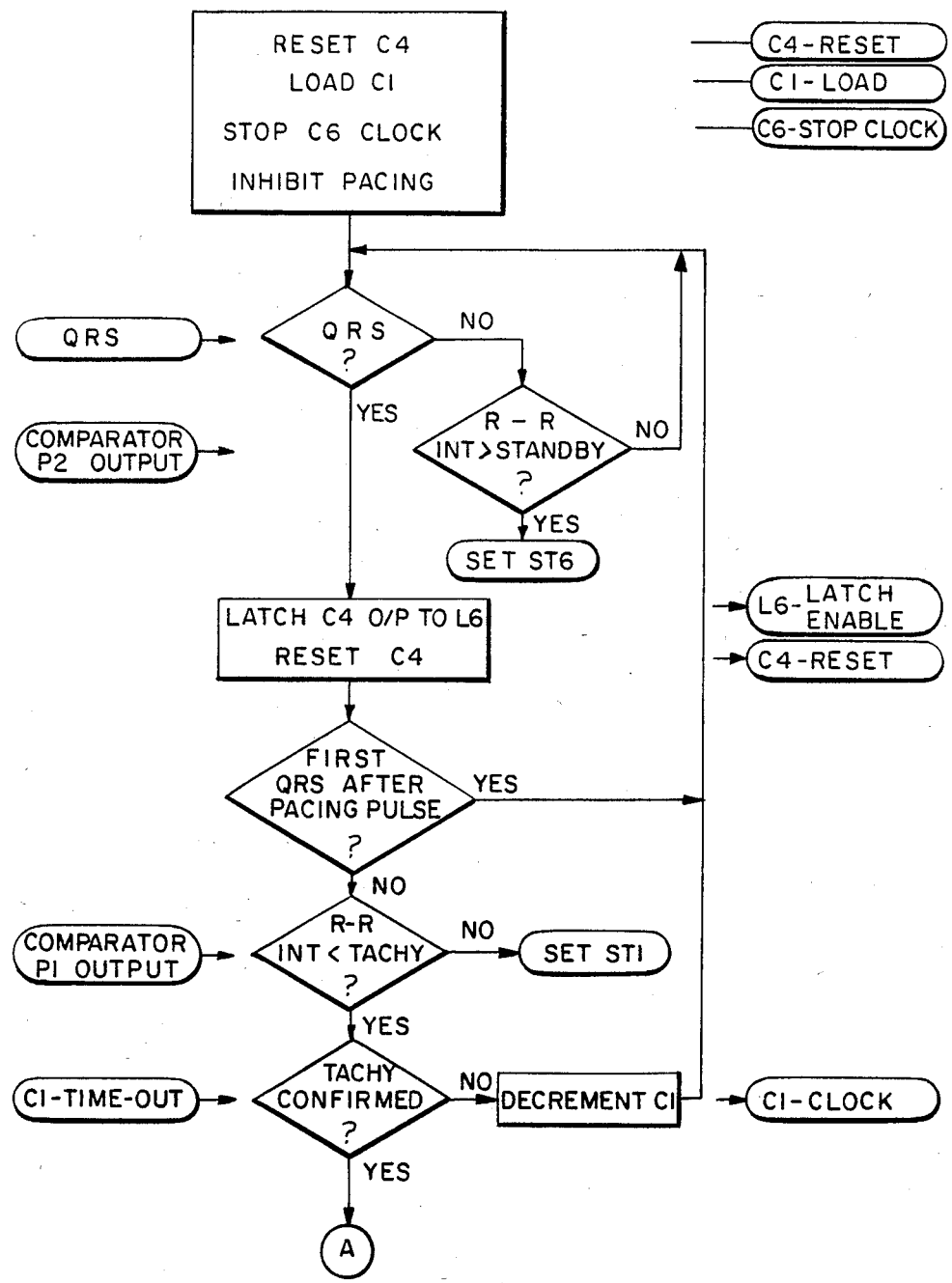

Referring to the flow chart of FIG. 11A, counter C4 is first reset when the system enters state ST4 or state ST5. At the end of the processing in both of states ST2 and ST3, a pacing pulse was generated or a heartbeat was sensed. As such, counter C4 is reset in order to time a new R—R interval Counter C1 is also loaded in preparation for another tachycardia confirmation process. It might be thought that there is no need to confirm tachycardia all over again, at least by the complete process of monitoring the full complement of fast heartbeats. Nevertheless, before taking any action it is preferable that the usual routine for confirming tachycardia be executed. There are no rigid rules which apply in all cases, and it is possible that a pulse which logically should not have terminated the tachycardia episode did so.

Furthermore, while the tachycardia episode may not have been terminated, even a single pacing pulse may have completely changed its timing. That is why, in the preferred embodiment of the invention, it is not enough simply to increment or decrement the old pacing interval. What must be done is to determine a new pacing interval based on the latest R—R interval in the tachycardia confirmation process. That interval will be used to access memory M1 to determine the appropriate pacing interval for use in the next phase A pacing. It is that new pacing interval which will be incremented or decremented, as will be described below, since it is now known that the plot of FIG. 2 is no longer applicable and that the plot has effectively moved upward or downward on the vertical scale.

The third step in the processing of FIG. 11A is to stop the 8-millisecond clock from decrementing counter C6. During processing in states ST4 and ST5, there are no pacing pulses generated. Rather, the system is set up for the generation of another pacing pulse in state ST6, or the generation of a phase A sequence in state ST2, or simple monitoring in state ST1. In fact, the fourth step in the processing of FIG. 11A is to inhibit pacing altogether.

It was a heartbeat which caused a transition to state ST4 or state ST5 in the first place. The system now waits for another heartbeat. As long as a heartbeat is not sensed, counter C4 continues to time the R—R interval. If the output of comparator P2 goes high to indicate that the heart has not beat for an interval exceeding the standby period, the system switches to state ST6. It is time for a pacing pulse because the heart has stopped beating.

In the usual case, however, a heartbeat will be sensed. The latch enable input of latch L6 is pulsed so that the latest R—R interval is latched. At the same time, counter C4 is reset to start the timing of another R—R interval.

The first R—R interval is ignored. The reason for this is that the first R—R interval after the generation of the last pacing pulse in a reversion sequence has been found not to be representative of a tachycardia episode. In this regard reference may be made to U.S. Pat. No. 4,427,011 which issued to Spurrell et al on Jan. 24, 1984. As indicated in FIG. 11A, the first QRS event which is sensed in state ST4 or state ST5 is ignored. The system goes back and waits for another QRS event.

For the next QRS event which is sensed, the output of comparator P1 is examined in the usual way. If the output stays low to indicate that the R—R interval is greater than the minimum interval stored in latch L1, it is an indication that the heart is beating in sinus rhythm. In other words, the heartbeat rate is not fast enough to be representative of tachycardia and it is not slow enough to require standby pacing. This is what is meant by the "sinus rhythm" conditions of FIG. 5. Whether the system is in state ST4 or state ST5, a transition is made to state ST1 as indicated in the state diagram and in FIG. 11A.

On the other hand, if the R—R interval is too short, the question is whether a sufficient number of consecutive short R—R intervals have occurred for the system to confirm that tachycardia still persists. Counter C1 is examined to see if it has timed out. It will be recalled that counter C1 is loaded with the number originally contained in latch L2 at the start of the processing in state ST4 or state ST5. If the counter has not timed out, it is simply decremented and the system continues to monitor heartbeats. A single beat in sinus rhythm during this monitoring causes a transition to state ST1, and a single inter-beat interval which exceeds the standby interval causes a transition to state ST6.

If counter C1 does eventually time out, it is an indication that tachycardia has been confirmed once again. The processing continues as shown on FIG. 11B, and one of two things happens depending upon whether the system is operating in state ST4 or state ST5.

The variable delta is decremented in state ST4 and incremented in state ST5. For example, suppose that in state ST2, while phase A pulses are being generated, an unevoked response is sensed. The pacing interval must be increased. The system transfers to state ST5 at which time delta is incremented from zero to one. (It is assumed this is the first pacing sequence after reprogramming and thus delta is zero.) This will cause the new pacing interval, after it is retrieved from memory M1 based on the most recent tachycardia cycle length, to be increased to reflect the fact that the plot of FIG. 2 must have moved upward. Suppose that when the system next transfers back to state ST2 for the actual generation of the second phase A sequence, another unevoked response is sensed, thus causing a second transfer to state ST5. In this state, delta will be incremented from one to two, thus causing twice the increase in the new pacing interval which will be used for the third phase A sequence.

On the other hand, the confirmation of tachycardia once the system has finished with phase A pacing and is engaged in phase B pacing is an indication that the new pacing interval, based on the most recent tachycardia cycle length, should be decreased because the plot of FIG. 2 must have shifted downward. As shown on FIG. 11B, delta is decremented; this will cause a reduction in the pacing interval used in the subsequent phase A sequence after the system transitions to state ST2. In a similar manner, continued cycling in the order ST2, ST3, ST4, ST2, ... will result in successive values for delta of 0, −1, −2, ....

It is possible that following a number of ST2-ST5 transitions, with delta being incremented each time, a phase A sequence is completed with the system entering state ST3. If a QRS is detected and tachycardia is then still confirmed, delta will be decremented in state ST4. It might then be decremented again in state ST4, or incremented in state ST5—after a pacing sequence of phase A or phase B is interrupted by a tachycardia QRS. The system hunts for an efficacious pacing interval, with delta not necessarily increasing or decreasing monotonically. The sign of delta at any time indicates whether the change to be made to a newly computed pacing interval is positive or negative; the magnitude of delta represents the degree of the change required. Each unit change in delta represents 8 milliseconds, ultimately controlled by the 8-millisecond clock input of counter C6. This means that counter C5 must be clocked once for each unit represented by delta.

Referring back to FIG. 11B, after delta is first incremented or decremented depending upon whether the system is in state ST4 or state ST5, counter C5 is loaded from memory M1 with a new pacing interval which corresponds to the last measured R—R interval. This is accomplished by pulsing the read input of the memory and the load input of the counter in the usual fashion. It is then that counter C5, representing the new pacing interval, is incremented or decremented depending on the current sign of delta. This is controlled by applying the appropriate potential level to the U/D (up/down) input of counter C5. Depending on the potential of this conductor, the counter is either incremented or decremented when its clock input is pulsed. The clock input is pulsed a number of times equal to the magnitude of delta. Once the adjusted pacing interval is set, counter C6 is loaded with it from counter C5. The clock input of counter C6 is then started so that the first pacing interval may be timed.

The system then switches to state ST2 so that phase A pulses may be generated. Since the tachycardia episode persists, another pacing pulse sequence is required.

It should be noted that the first processing in state ST2, as depicted on FIG. 9, is the decrementing of clock C3 and then the checking whether the maximum number of attempts at terminating the tachycardia have already been made. It is only after the tachycardia has been terminated, and the system ultimately finds itself in state ST1, that counter C3 is loaded from latch L4 so that the maximum number of attempts may be made once again the next time that tachycardia is confirmed.

STATE ST6—FIG. 12

As mentioned above, practically the only thing that happens in state ST6 is that a single pacing pulse is generated following the current R—R interval exceeding the standby interval. Before the pacing pulse is generated, as indicated on FIG. 12, the input of the sense module is blanked, typically for 100 milliseconds, so that only unevoked responses will be sensed by the sense amplifier. After pacing, the system switches to state ST1 where the cycle begins all over again with the monitoring of heartbeats.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:
1. A method of operating a tachycardia control pacer comprising the steps of:
    (a) sensing and monitoring the rate of successive patient heartbeats to confirm the existence of a tachycardia episode,
    (b) determining a pacing interval as a predetermined function of the rate at which the patient heartbeats are occurring, said predetermined function being based upon the physiological relationship of effective refractory period and tachycardia rate, and
    (c) generating a sequence of pacing pulses at intervals equal to said pacing interval in order to terminate said tachycardia episode, with the first pacing pulse of said sequence being generated following the last heartbeat used to confirm the tachycardia episode after the elapse of an interval which is equal to said pacing interval.
2. A method of operating a tachycardia control pacer in accordance with claim 1 wherein said pacing interval increases with a decreasing patient heartbeat rate but with a decreasing slope.
3. A method of operating a tachycardia control pacer in accordance with claim 2 wherein at relatively fast tachycardia rates the pacing interval is only slightly less than the intervals between heartbeats, and at relatively slow tachycardia rates the pacing interval is approximately half of the intervals between heartbeats.
4. A method of operating a tachycardia control pacer in accordance with claim 2 wherein the tachycardia control pacer has stored therein a table representing said predetermined function, and said pacing interval is determined in step (b) by a process of interpolation.
5. A method of operating a tachycardia control pacer in accordance with claim 4 wherein said predetermined function is empirically determined based upon experiments performed on a sample population.
6. A method of operating a tachycardia control pacer in accordance with claim 1 wherein said predetermined function is empirically determined based upon experiments performed on a sample population.

7. A method of operating a tachycardia control pacer in accordance with claim 6 wherein said experiments include the steps of (i) pacing a sample patient population at each of many rates, (ii) for each rate and for each patient, scanning the last pacing interval to determine the effective refractory interval for the respective patient-rate pair, (iii) averaging the data determined in step (ii) to compute a function of effective refractory period versus rate, and (iv) calculating said predetermined function by selecting a pacing interval for each rate which is slightly greater than the respective effective refractory period computed in step (iii) for the same rate.

8. A method of operating a tachycardia control pacer in accordance with claim 1 wherein if any heartbeat sensed during said sequence of pacing pulses generated in step (c) is not an evoked response, step (c) is repeated but with an incremented pacing interval.

9. A method of operating a tachycardia control pacer in accordance with claim 8 wherein step (c) is repeated with an incremented pacing interval only after step (a) is repeated once again to confirm that the tachycardia episode still exists.

10. A method of operating a tachycardia control pacer in accordance with claim 9 wherein if any heartbeat sensed during said sequence of pacing pulses generated in step (c) is not an evoked response, step (c) is immediately aborted.

11. A method of operating a tachycardia control pacer in accordance with claim 8 wherein step (c) is repeated only after step (a) is first repeated to confirm that the tachycardia episode still exists and step (b) is also repeated to determine a new pacing interval, with the pacing interval used in the repeated step (c) being equal to the determined new pacing interval plus an increment.

12. A method of operating a tachycardia control pacer in accordance with claim 11 wherein if any heartbeat sensed during said sequence of pacing pulses generated in step (c) is not an evoked response, step (c) is immediately aborted.

13. A method of operating a tachycardia control pacer in accordance with claim 1 further including the step of:
(d) in the event no unevoked heartbeat is sensed during said sequence of pacing pulses generated in step (c), generating a second sequence of pacing pulses in which the intervals between successive pulses successively lengthen.

14. A method of operating a tachycardia control pacer in accordance with claim 13 wherein step (a) is executed to determine whether the tachycardia episode still exists following the sensing of an unevoked heartbeat after the generation of at least one of the pacing pulses in the second sequence of step (d), and if the tachycardia episode still exists then repeating step (c) with a decremented pacing interval.

15. A method of operating a tachycardia control pacer in accordance with claim 14 wherein step (d) is aborted immediately and step (a) is executed responsive to the beating of the patient's heart following the last pacing pulse within an interval which exceeds a prestored blanking interval but is less than a prestored standby interval.

16. A method of operating a tachycardia control pacer in accordance with claim 14 wherein, prior to the repeating of step (c), step (b) is first repeated to determine a new pacing interval, with the pacing interval used in the repeated step (c) being equal to the determined new pacing interval less a decrement.

17. A method of operating a tachycardia control pacer in accordance with claim 16 wherein step (d) is aborted immediately and steps (a) and (b) are executed responsive to the beating of the patient's heart following the last pacing pulse within an interval which exceeds a prestored blanking interval but is less than a prestored standby interval.

18. A method of operating a tachycardia control pacer in accordance with claim 1 wherein the same electrode is used in steps (a) and (c).

19. A method of operating a tachycardia control pacer comprising the steps of:
(a) sensing and monitoring the rate of successive patient heartbeats to confirm the existence of a tachycardia episode,
(b) determining a sequence of pacing pulses whose inter-pulse intervals are a predetermined function of the rate at which the patient heartbeats are occurring, said predetermined function being based upon the physiological relationship of effective refractory period and tachycardia rate, and
(c) generating said sequence of pacing pulses at the rate associated with said inter-pulse intervals.

20. A method of operating a tachycardia control pacer in accordance with claim 19 wherein the rate of said pacing pulse sequence decreases with a decreasing patient heartbeat rate and with a decreasing slope.

21. A method of operating a tachycardia control pacer in accordance with claim 20 wherein at relatively fast tachycardia rates the pacing pulse rate is only slightly greater than the heartbeat rate, and at relatively slow tachycardia rates the pacing pulse rate is approximately twice the heartbeat rate.

22. A method of operating a tachycardia control pacer in accordance with claim 20 wherein the tachycardia control pacer has stored therein a table representing said predetermined function, and said inter-pulse intervals are determined in step (b) by a process of interpolation.

23. A method of operating a tachycardia control pacer in accordance with claim 19 wherein said predetermined function is empirically determined based upon experiments performed on a sample population.

24. A method of operating a tachycardia control pacer in accordance with claim 23 wherein, said experiments include the steps of (i) pacing a sample patient population at each of many rates, (ii) for each rate and for each patient, scanning the last pacing interval to determine the effective refractory interval for the respective patient-rate pair, (iii) averaging the data determined in step (ii) to compute a function of effective refractory period versus rate, and (iv) calculating said predetermined function by selecting a pacing pulse rate for each experimental rate which is slightly less than the inverse of the respective effective refractory period computed in step (iii) for the same experimental rate.

25. A method of operating a tachycardia control pacer in accordance with claim 19 wherein if any heartbeat sensed during said sequence of pacing pulses generated in step (c) is not an evoked response, step (c) is repeated but with a decremented pacing pulse rate.

26. A method of operating a tachycardia control pacer in accordance with claim 25, wherein step (c) is repeated with a slower pacing pulse rate only after step (a) is repeated once again to confirm that the tachycardia episode still exists.

27. A method of operating a tachycardia control pacer in accordance with claim 26 wherein if any heartbeat sensed during said sequence of pacing pulses generated in step (c) is not an evoked response, step (c) is immediately aborted.

28. A method of operating a tachycardia control pacer in accordance with claim 25 wherein step (c) is repeated only after step (a) is first repeated to confirm that the tachycardia episode still exists and step (b) is also repeated to determine a new pacing rate, with the pacing rate used in the repeated step (c) being slightly less than the determined new pacing rate.

29. A method of operating a tachycardia control pacer in accordance with claim 28 wherein if any heartbeat sensed during said sequence of pacing pulses generated in step (c) is not an evoked response, step (c) is immediately aborted.

30. A method of operating a tachycardia control pacer in accordance with claim 19 further including the step of:
(d) in the event no unevoked heartbeat is sensed during said sequence of pacing pulses generated in step (c), generating a second sequence of pacing pulses in which the rate continuously decreases.

31. A method of operating a tachycardia control pacer in accordance with claim 30 wherein step (a) is executed to determine whether the tachycardia episode still exists following the sensing of an unevoked heartbeat after the generation of at least one of the pacing pulses in the second sequence of step (d), and if the tachycardia episode still exists then repeating step (c) with an incremented pacing pulse rate.

32. A method of operating a tachycardia control pacer in accordance with claim 31 wherein step (d) is aborted immediately and step (a) is executed responsive to the beating of the patient's heart following the last pacing pulse within an interval which exceeds a prestored blanking interval but is less than a prestored standby interval.

33. A method of operating a tachycardia control pacer in accordance with claim 31 wherein, prior to the repeating of step (c), step (b) is first repeated to determine a new pacing pulse rate, with the pacing pulse rate used in the repeated step (c) being slightly greater than the determined new pacing pulse rate.

34. A method of operating a tachycardia control pacer in accordance with claim 33 wherein step (d) is aborted immediately and steps (a) and (b) are executed responsive to the beating of the patient's heart following the last pacing pulse within an interval which exceeds a prestored blanking interval but is less than a prestored standby interval.

35. A method of operating a tachycardia control pacer in accordance with claim 19 wherein the same electrode is used in steps (a) and (c).

36. A method of operating a tachycardia control pacer comprising the steps of:
(a) sensing and monitoring the rate of successive patient heartbeats to confirm the existence of a tachycardia episode,
(b) determining a pacing interval which is a function of the rate at which the patient heartbeats are occurring,
(c) generating a sequence of pacing pulses at intervals equal to said pacing interval in order to terminate said tachycardia episode, with the first pacing pulse of said sequence being generated following the last heartbeat used to confirm the tachycardia episode after the elapse of an interval which is equal to said pacing interval, and
(d) in the event no unevoked heartbeat is sensed during said sequence of pacing pulses generated in step (c), generating a second sequence of pacing pulses in which the intervals between successive pulses successively lengthen.

37. A method of operating a tachycardia control pacer in accordance with claim 36, wherein step (d) is merged into standby pacing as the intervals between pacing pulses in said second sequence successively lengthen, and further including the steps of:
(e) sensing an unevoked heartbeat after the generation of at least one pacing pulse in the second sequence of step (d),
(f) in response to the sensing of an unevoked heartbeat in step (e), executing step (a) to determine whether the tachycardia episode still exists, and
(g) in response to determining in step (f) that the tachycardia episode still exists, repeating step (c) but with a decremented pacing interval.

38. A method of operating a tachycardia control pacer in accordance with claim 37 wherein step (d) is aborted and step (f) is executed immediately responsive to the sensing of a heartbeat in step (e).

39. A method of operating a tachycardia control pacer in accordance with claim 38, wherein, prior to the repeating of step (c), step (b) is first repeated to determine a new pacing interval, with the pacing interval used in the repeated step (c) being equal to the determined new pacing interval less a decrement.

40. A method of operating a tachycardia control pacer in accordance with claim 36 wherein said pacing interval of step (b) increases with a decreasing patient heartbeat rate but with a decreasing slope.

41. A method of operating a tachycardia control pacer in accordance with claim 40 wherein at relatively fast tachycardia rates the pacing interval is only slightly less than the intervals between heartbeats, and at relatively slow tachycardia rates the pacing interval is approximately half of the intervals between heartbeats.

42. A method of operating a tachycardia control pacer in accordance with claim 36 wherein said function of step (b) is predetermined, the tachycardia control pacer has stored therein a table representing said function, and said pacing interval is determined in step (b) by a process of interpolation.

43. A method of operating a tachycardia control pacer in accordance with claim 36 wherein said function of step (b) is empirically determined based upon experiments performed on a sample population.

44. A method of operating a tachycardia control pacer in accordance with claim 43 wherein said experiments include the steps of (i) pacing a sample patient population at each of many rates, (ii) for each rate and for each patient, scanning the last pacing interval to determine the effective refractory interval for the respective patient-rate pair, (iii) averaging the data determined in step (ii) to compute a function of effective refractory period versus rate, and (iv) calculating said function by selecting a pacing interval for each rate which is slightly greater than the respective effective refractory period computed in step (iii) for the same rate.

45. A method of operating a tachycardia control pacer in accordance with claim 36 wherein if any heartbeat sensed during said sequence of pacing pulses generated in step (c) is not an evoked response, step (c) is repeated but with an incremented pacing interval.

46. A method of operating a tachycardia control pacer in accordance with claim 45 wherein step (c) is repeated with an incremented pacing interval only after step (a) is repeated once again to confirm that the tachycardia episode still exists.

47. A method of operating a tachycardia control pacer in accordance with claim 45 wherein if any heartbeat sensed during said sequence of pacing pulses generated in step (c) is not an evoked response, step (c) is immediately aborted.

48. A method of operating a tachycardia control pacer in accordance with claim 45 wherein step (c) is repeated only after step (a) is first repeated to confirm that the tachycardia episode still exists and step (b) is also repeated to determine a new pacing interval, with the pacing interval used in the repeated step (c) being equal to the determined new pacing interval plus an increment.

49. A method of operating a tachycardia control pacer in accordance with claim 48 wherein if any heartbeat sensed during said sequence of pacing pulses generated in step (c) is not an evoked response, step (c) is immediately aborted.

50. A method of operating a tachycardia control pacer in accordance with claim 36 wherein the same electrode is used in steps (a) and (c).

51. A method of operating a tachycardia control pacer comprising the steps of:
  (a) sensing and monitoring the rate of successive patient heartbeats to confirm the existence of a tachycardia episode,
  (b) generating a sequence of pacing pulses at intervals which are a function of the effective refractory period intrinsically associated with the rate of the heartbeats sensed in step (a), and
  (c) in the event no unevoked heartbeat is sensed during said sequence of pacing pulses generated in step (b), generating a second sequence of pacing pulses in which the intervals between successive pulses successively lengthen.

52. A method of operating a tachycardia control pacer in accordance with claim 51 wherein step (c) is merged into standby pacing as the intervals between pacing pulses in said second sequence successively lengthen, and further including the steps of:
  (d) sensing an unevoked heartbeat after the generation of at least one pacing pulse in the second sequence of step (c),
  (e) in response to the sensing of an unevoked heartbeat in step (d), executing step (a) to determine whether the tachycardia episode still exists, and
  (f) in response to determining in step (e) that the tachycardia episode still exists, repeating step (b) but with decremented pacing intervals.

53. A method of operating a tachycardia control pacer in accordance with claim 52 wherein step (c) is aborted and step (e) is executed immediately responsive to the sensing of a heartbeat in step (d).

54. A method of operating a tachycardia control pacer in accordance with claim 51 wherein said intervals of step (b) increase as a function of a decreasing patient heartbeat rate but with a decreasing slope.

55. A method of operating a tachycardia control pacer in accordance with claim 54 wherein at relatively fast tachycardia rates the intervals of step (b) are only slightly less than the intervals between heartbeats, and at relatively slow tachycardia rates the intervals of step (b) are approximately half of the intervals between heartbeats.

56. A method of operating a tachycardia control pacer in accordance with claim 51 wherein said function of step (b) is predetermined, the tachycardia control pacer has stored therein a table representing said function, and said pacing intervals are determined in step (b) by a process of interpolation.

57. A method of operating a tachycardia control pacer in accordance with claim 51 wherein said function of step (b) is empirically determined based upon experiments performed on a sample population.

58. A method of operating a tachycardia control pacer in accordance with claim 57 wherein said experiments include the steps of (i) pacing a sample patient population at each of many rates, (ii) for each rate and for each patient, scanning the last pacing interval to determine the effective refractory interval for the respective patient-rate pair, (iii) averaging the data determined in step (ii) to compute a function of effective refractory period versus rate, and (iv) calculating said function by selecting pacing intervals for each rate which are slightly greater than the respective effective refractory period computed in step (iii) for the same rate.

59. A method of operating a tachycardia control pacer in accordance with claim 51 wherein if any heartbeat sensed during said sequence of pacing pulses generated in step (b) is not an evoked response, step (b) is repeated but with incremented pacing intervals.

60. A method of operating a tachycardia control pacer in accordance with claim 59 wherein step (b) is repeated with incremented pacing intervals only after step (a) is repeated once again to confirm that the tachycardia episode still exists.

61. A method of operating a tachycardia control pacer in accordance with claim 60 wherein if any heartbeat sensed during said sequence of pacing pulses generated in step (b) is not an evoked response, step (b) is immediately aborted.

62. A method of operating a tachycardia control pacer in accordance with claim 51 wherein the same electrode is used in steps (a) and (b).

63. A method of operating a tachycardia control pacer comprising the steps of:
  (a) sensing successive patient heartbeats to confirm the existence of a tachycardia episode, and
  (b) generating a sequence of pacing pulses at intervals which are a function of the effective refractory period intrinsically associated with the rate of the heartbeats sensed in step (a).

64. A method of operating a tachycardia control pacer in accordance with claim 63 further including the step of:
  (c) in the event no unevoked heartbeat is sensed during said sequence of pacing pulses generated in step (b), generating a second sequence of pacing pulses in which the intervals between successive pulses successively lengthen so that they merge into standby pacing,
  (d) sensing an unevoked heartbeat after the generation of at least one pacing pulse in the second sequence of step (c),
  (e) in response to the sensing of an unevoked heartbeat in step (d), executing step (a) to determine whether the tachycardia episode still exists, and (f) in response to determining in step (e) that the tachycardia episode still exists, repeating step (b) but with decremented pacing intervals.

65. A method of operating a tachycardia control pacer in accordance with claim 64 wherein step (c) is aborted and step (e) is executed immediately responsive to the sensing of a heartbeat in step (d).

66. A method of operating a tachycardia control pacer in accordance with claim 63 wherein said intervals of step (b) increase as a function of a decreasing patient heartbeat rate but with a decreasing slope.

67. A method of operating a tachycardia control pacer in accordance with claim 66 wherein at relatively fast tachycardia rates the intervals of step (b) are only slightly less than the intervals between heartbeats, and at relatively slow tachycardia rates the intervals of step (b) are approximately half of the intervals between heartbeats.

68. A method of operating a tachycardia control pacer in accordance with claim 63 wherein said function of step (b) is predetermined, the tachycardia control pacer has stored therein a table representing said function, and said pacing intervals are determined in step (b) by a process of interpolation.

69. A method of operating a tachycardia control pacer in accordance with claim 63 wherein said function of step (b) is empirically determined based upon experiments performed on a sample population.

70. A method of operating a tachycardia control pacer in accordance with claim 68 wherein said experiments include the steps of (i) pacing a sample patient population at each of many rates, (ii) for each rate and for each patient, scanning the last pacing interval to determine the effective refractory interval for the respective patient-rate pair, (iii) averaging the data determined in step (ii) to compute a function of effective refractory period versus rate, and (iv) calculating said function by selecting pacing intervals for each rate which are slightly greater than the respective effective refractory period computed in step (iii) for the same rate.

71. A method of operating a tachycardia control pacer in accordance with claim 63 wherein if any heartbeat sensed during said sequence of pacing pulses generated in step (b) is not an evoked response, step (b) is repeated but with incremented pacing intervals.

72. A method of operating a tachycardia control pacer in accordance with claim 71 wherein step (b) is repeated with incremented pacing intervals only after step (a) is repeated once again to conrirm that the tachycardia episode still exists.

73. A method of operating a tachycardia control pacer in accordance with claim 72 wherein if any heartbeat sensed during said sequence of pacing pulses generated in step (b) is not an evoked response, step (b) is immediately aborted.

74. A method of operating a tachycardia control pacer in accordance with claim 73 further including the step of:
(c) in the event no unevoked heartbeat is sensed during said sequence of pacing pulses generated in step (b), generating a second sequence of pacing pulses in which the intervals between successive pulses successively lengthen so that they merge into standby pacing,
(d) sensing an unevoked heartbeat after the generation of at least one pacing pulse in the second sequence of step (c),
(e) in response to the sensing of an unevoked heartbeat in step (d), executing step (a) to determine whether the tachycardia episode still exists, and
(f) in response to determining in step (e) that the tachycardia episode still exists, repeating step (b) but with decremented pacing intervals.

75. A method of operating a tachycardia control pacer in accordance with claim 74 wherein step (c) is aborted and step (e) is executed immediately responsive to the sensing of a heartbeat in step (d).

76. A method of operating a tachycardia control pacer in accordance with claim 72 further including the step of:
(c) in the event no unevoked heartbeat is sensed during said sequence of pacing pulses generated in step (b), generating a second sequence of pacing pulses in which the intervals between successive pulses successively lengthen so that they merge into standby pacing,
(d) sensing an unevoked heartbeat after the generation of at least one pacing pulse in the second sequence of step (c),
(e) in response to the sensing of an unevoked heartbeat in step (d), executing step (a) to determine whether the tachycardia episode still exists, and
(f) in response to determining in step (e) that the tachycardia episode still exists, repeating step (b) but with decremented pacing intervals.

77. A method of operating a tachycardia control pacer in accordance with claim 76 wherein step (c) is aborted and step (e) is executed immediately responsive to the sensing of a heartbeat in step (d).

78. A method of operating a tachycardia control pacer in accordance with claim 63 wherein the same electrode is used in steps (a) and (b).

79. A method of operating a tachycardia control pacer comprising the steps of:
(a) sensing and monitoring the rate of successive patient heartbeats to confirm the existence of a tachycardia episode,
(b) determining a pacing interval which is a function of the rate at which the patient heartbeats are occurring,
(c) generating a sequence of pacing pulses at intervals equal to said pacing interval in order to terminate said tachycardia episode, with the first pacing pulse of said sequence being generated following the last heartbeat used to confirm the tachycardia episode after the elapse of an interval which is equal to said pacing interval, and
(d) repeating step (c) until the tachycardia episode is terminated but modifying the pacing interval used for each pacing pulse sequence by
  (i) increasing it if at least one unevoked heartbeat is sensed during the preceding pacing pulse sequence, or
  (ii) decreasing it in the absence of any unevoked heartbeat during the preceding pacing pulse sequence.

80. A method of operating a tachycardia control pacer in accordance with claim 79 wherein said pacing interval determined in step (b) increases with a decreasing patient heartbeat rate but with a decreasing slope.

81. A method of operating a tachycardia control pacer in accordance with claim 80 wherein at relatively fast tachycardia rates the pacing interval is only slightly less than the intervals betweeh heartbeats, and at relatively slow tachycardia rates the pacing interval is approximately half of the intervals between heartbeats.

82. A method of operating a tachycardia control pacer in accordance with claim 80 wherein the tachycardia control pacer has stored therein a table representing a predetermined function, and said pacing interval is determined in step (b) by a process of interpolation.

83. A method of operating a tachycardia control pacer in accordance with claim 79 wherein step (c) is repeated with an increased pacing interval only after step (a) is repeated once again to confirm that the tachycardia episode still exists.

84. A method of operating a tachycardia control pacer in accordance with claim 79 wherein step (c) is repeated with a decreased pacing interval only after step (a) is repeated once again to confirm that the tachycardia episode still exists.

85. A method of operating a tachycardia control pacer in accordance with claim 79 wherein if any heartbeat sensed during said sequence of pacing pulses generated in step (c) is not an evoked response, step (c) is immediately aborted and step (d) is executed.

86. A method of operating a tachycardia control pacer in accordance with claim 79 wherein step (c) is repeated only after step (a) is first repeated to confirm that the tachycardia episode still exists and step (b) is also repeated to determine a new pacing interval, with the pacing interval used in the repeated step (c) being equal to the determined new pacing interval plus an increment or less a decrement.

87. A method of operating a tachycardia control pacer in accordance with claim 86 further including the step of:
(e) in the event no unevoked heartbeat is sensed during said sequence of pacing pulses generated in step (c), generating a second sequence of pacing pulses in which the intervals between successive pulses successively lengthen.

88. A method of operating a tachycardia control pacer in accordance with claim 87 wherein the same electrode is used in steps (a) and (c).

89. A method of operating a tachycardia control pacer in accordance with claim 79 further including the step of:
(e) in the event no unevoked heartbeat is sensed during said sequence of pacing pulses generated in step (c), generating a second sequence of pacing pulses in which the intervals between successive pulses successively lengthen.

90. A method of operating a tachycardia control pacer in accordance with claim 79 wherein the same electrode is used in steps (a) and (c).

91. A method of operating a tachycardia control pacer comprising the steps of:
(a) sensing and monitoring the rate of successive patient heartbeats to confirm the existence of a tachycardia episode,
(b) determining a pacing rate which is a function of the rate at which the patient heartbeats are occurring,
(c) generating a sequence of pacing pulses at said pacing rate in order to terminate said tachycardia episode, and
(d) repeating step (c) until the tachycardia episode is terminated but modifying the pacing rate used for each pacing pulse sequence by (i) decreasing it if at least one unevoked heartbeat is sensed during the preceding pacing pulse sequence, or
(ii) increasing it in the absence of any unevoked heartbeat during the preceding pacing pulse sequence.

92. A method of operating a tachycardia control pacer in accordance with claim 91 wherein said pacing rate determined in step (b) decreases with a decreasing patient heartbeat rate and with a decreasing slope.

93. A method of operating a tachycardia control pacer in accordance with claim 91 wherein the tachycardia control pacer has stored therein a table representing a predetermined function, and said pacing rate is determined in step (b) by a process of interpolation.

94. A method of operating a tachycardia control pacer in accordance with claim 91 wherein step (c) is repeated with a decreased pacing rate/only after step (a) is repeated once again to confirm that the tachycardia episode still exists.

95. A method of operating a tachycardia control pacer in accordance with claim 94 wherein step (c) is repeated with an increased pacing rate only after step (a) is repeated once again to confirm that the tachycardia episode still exists.

96. A method of operating a tachycardia control pacer in accordance with claim 91 wherein if any heartbeat sensed during said sequence of pacing pulses generated in step (c) is not an evoked response, step (c) is immediately aborted and step (d) is executed.

97. A method of operating a tachycardia control pacer in accordance with claim 91 wherein step (c) is repeated only after step (a) is first repeated to confirm that the tachycardia episode still exists and step (b) is also repeated to determine a new pacing rate, with the pacing rate used in the repeated step (c) being equal to the determined new pacing rate plus an increment or less a decrement.

98. A method of operating a tachycardia control pacer in accordance with claim 97 further including the step of:
(e) in the event no unevoked heartbeat is sensed during said sequence of pacing pulses generated in step (c), generating a second sequence of pacing pulses in which the pacing rate continuously decreases.

99. A method of operating a tachycardia control pacer in accordance with claim 91 further including the step of:
(e) in the event no unevoked heartbeat is sensed during said sequence of pacing pulses generated in step (c), generating a second sequence of pacing pulses in which the pacing rate continuously decreases.

100. A method of operating a tachycardia control pacer in accordance with claim 91 wherein the same electrode is used in steps (a) and (c).

101. A method of operating a tachycardia control pacer comprising the steps of:
(a) monitoring the rate of successive patient heartbeats to confirm the existence of a tachycardia episode,
(b) determining a pacing interval which is a function of the rate at which the patient heartbeats are occurring,
(c) generating a sequence of pacing pulses at intervals equal to said pacing interval in order to terminate said tachycardia episode, with the first pacing pulse of said sequence being generated following the last heartbeat used to confirm the tachycardia episode after the elapse of an interval which is equal to said pacing interval, and (d) repeating step (c) until the tachycardia episode is terminated and preceding each repetition of step (c) by a repetition of step (b), but calculating successive pacing intervals for use in successive repetitions of step (c) by changing the pacing interval determined in step (b) by a predetermined amount.

102. A method of operating a tachycardia control pacer in accordance with claim 101 wherein each repetition of step (c) is preceded by a repetition of step (a) prior to the repetition of step (b).

103. A method of operating a tachycardia control pacer in accordance with claim 101 wherein if any heartbeat sensed during said sequence of pacing pulses generated in step (c) is not an evoked response, step (c) is immediately aborted and step (d) is executed.

104. A method of operating a tachycardia control pacer in accordance with claim 101 wherein step (c) is repeated only after step (a) is first, repeated to confirm that the tachycardia episode still exists before step (b) is also repeated to determine a new pacing interval, with the pacing interval used in the repeated step (c) being equal to the determined new pacing interval changed by a predetermined amount.

105. A method of operating a tachycardia control pacer in accordance with claim 101 further including the step of:

(e) in the event no unevoked heartbeat is sensed during said sequence of pacing pulse generated in step (c), generating a second sequence of pacing pulses in which the intervals between successive pulses successively lengthen.

106. A method of operating a tachycardia control pacer comprising the steps of:

(a) sensing successive patient heartbeats to confirm the existence of a tachycardia episode, (b) determining pacing intervals which are a function of the rate at which the patient heartbeats are occurring, (c) generating a sequence of pacing pulses at the determined pacing intervals in order to terminate said tachycardia episode, and (d) repeating step (c) until the tachycardia episode is terminated and preceding each repetition of step (c) by a repetition of step (b), but calculating successive pacing intervals for use in successive repetitions of step (c) by changing the pacing interval determined in step (b) by predetermined amounts.

107. A method of operating a tachycardia control pacer in accordance with claim 106 wherein each repetition of step (c) is preceded by a repetition of step (a) prior to the repetition of step (b).

108. A method of operating a tachycardia control pacer in accordance with claim 106 wherein if any heartbeat sensed during said sequence of pacing pulses generated in step (c) is not an evoked response, step (c) is immediately aborted and step (d) is executed.

109. A method of operating a tachycardia control pacer in accordance with claim 106 wherein step (c) is repeated only after step (a) is first repeated to confirm that the tachycardia episode still exists before step (b) is also repeated to determine new pacing intervals, with the pacing intervals used in the repeated step (c) being equal to the determined new pacing intervals changed by a predetermined amount.

110. A method of operating a tachycardia control pacer in accordance with claim 106 further including the step of:

(e) in the event no unevoked heartbeat is sensed during said sequence of pacing pulses generated in step (c), generating a second sequence of pacing pulses in which the intervals between successive pulses successively lengthen.

111. A method of operating a tachycardia control pacer comprising the steps of:

(a) sensing successive patient heartbeats to confirm the existence of a tachycardia episode, (b) determining pacing intervals which are a function of the rate at which the patient heartbeats are occurring, (c) generating a sequence of pacing pulses at the determined pacing intervals in order to terminate said tachycardia episode, (d) blanking the sensing of patient heartbeats for a predetermined interval following the generation of each pacing pulse in step (c), and (e) responsive to the sensing of a patient heartbeat during the execution of step (c), repeating step (c) but with longer pacing intervals.

112. A method of operating a tachycardia control pacer in accordance with claim 111 wherein said function is predetermined and empirically determined based upon experiments performed on a sample population.

113. A method of operating a tachycardia control pacer in accordance with claim 112 wherein said experiments include the steps of (i) pacing a sample patient population at each of many rates, (ii) for each rate and for each patient, scanning the last pacing interval to determine the effective refractory interval for the respective patient-rate pair, (iii) averaging the data determined in step (ii) to compute a function of effective refractory period versus rate, and (iv) calculating said predetermined function by selecting pacing intervals for each rate which are slightly greater than the respective effective refractory period computed in step (iii) for the same rate.

114. A method of operating a tachycardia control pacer in accordance with claim 111 wherein step (c) is repeated with longer pacing intervals only after step (a) is repeated once again to confirm that the tachycardia episode still exists.

115. A method of operating a tachycardia control pacer in accordance with claim 111 wherein step (c) is repeated only after step (a) is first repeated to confirm that the tachycardia episode still exists and step (b) is also repeated to determine new pacing intervals, with the pacing intervals used in the repeated step (c) being equal to the determined new pacing intervals plus an increment.

116. A method of operating a tachycardia control pacer in accordance with claim 115 further including the step of:

(f) in the event a patient heartbeat is not sensed during said sequence of pacing pulses generated in step (c), generating a second sequence of pacing pulses in which the intervals between successive pulses successively lengthen.

117. A method of operating a tachycardia control pacer in accordance with claim 116 wherein step (a) is executed to determine whether the tachycardia episode still exists following the sensing of a patient heartbeat after the generation of at least one of the pacing pulses in the second sequence of step (f), and if the tachycardia episode still exists then repeating step (c) with shorter pacing intervals.

118. A method of operating a tachycardia control pacer in accordance with claim 117 wherein, prior to the repeating of step (c), following step (f), step (b) is first repeated to determine new pacing intervals, with the pacing intervals used in the repeated step (c) being equal to the determined new pacing intervals less a decrement.

119. A method of operating a tachycardia control pacer in accordance with claim 111 further including the step of:

(f) in the event a patient heartbeat is not sensed during said sequence of pacing pulses generated in step (c), generating a second sequence of pacing pulses in which the intervals between successive pulses successively lengthen.

120. A method of operating a tachycardia control pacer in accordance with claim 119 wherein step (a) is executed to determine whether the tachycardia episode still exists following the sensing of a patient heartbeat after the generation of at least one of the pacing pulses in the second sequence of step (f), and if the tachycardia episode still exists then repeating step (c) with shorter pacing intervals.

121. A method of operating a tachycardia control pacer in accordance with claim 120 wherein, prior to the repeating of step (c), following step (f), step (b) is first repeated to determine new pacing intervals, with the pacing intervals used in the repeated step (c) being equal to the determined new pacing intervals less a decrement.

122. A method of operating a tachycardia control pacer in accordance with claim 111 wherein the same electrode is used in steps (a) and (c).

* * * * *